(12) United States Patent
Huang et al.

(10) Patent No.: US 8,143,483 B2
(45) Date of Patent: Mar. 27, 2012

(54) GENES FOR PROMOTING PLANT GROWTH AND USE THEREOF

(75) Inventors: Pung-Ling Huang, Taipei (TW); Yi-Yin Do, Taipei (TW); Meng-Jin Lin, Taipei (TW)

(73) Assignee: National Taiwan University, Taipei (TW)

( * ) Notice: Subject to any disclaimer, the term of this patent is extended or adjusted under 35 U.S.C. 154(b) by 144 days.

(21) Appl. No.: 12/610,064

(22) Filed: Oct. 30, 2009

(65) Prior Publication Data
US 2011/0107462 A1     May 5, 2011

(51) Int. Cl.
*A01H 5/00*     (2006.01)

(52) U.S. Cl. ........ 800/290; 536/23.6; 435/419; 435/468

(58) Field of Classification Search .................. None
See application file for complete search history.

(56) References Cited

U.S. PATENT DOCUMENTS
6,858,774 B2 *  2/2005  Spalding et al. .............. 800/278

OTHER PUBLICATIONS

Crouzet et al (FEBS Letters 580 (2006) 1123-1130).*
Biemans-Oldehinkel, et al, ABC transporter architecture and regulatory roles of accessory domains, Journal: FEBS Letters, pp. 1023-1035, Volume-issue No. 580, 2006.
Higgins, C. F., ABC transporter from microorganisms to man, Journal: Annu. Rev. Cell Biol., pp. 67-113, Volume-issue No. 8, 1992.
Schutzendu Bel, A. et al, Cadmium-induced changes in antioxidative systems, hydrogen peroxide content, and differentiation in Scots pine roots, Journal: Plant Physiology, pp. 887-898, Volume-issue No. 127, 2001.

* cited by examiner

*Primary Examiner* — Anne Marie Grunberg
*Assistant Examiner* — Lee Visone
(74) *Attorney, Agent, or Firm* — WPAT, P.C.; Anthony King

(57) ABSTRACT

The invention relates to genes for promoting rapid growth of plant, characterized in genes that are Banana ABC transporter MhPDR1 or MhPDR2 genes, wherein the transporters have amino acid sequences depicted in SEQ ID No: 1 and SEQ ID No: 3, respectively, and the genes have nucleotide sequences depicted in SEQ ID No: 2 and SEQ ID No: 4, respectively. The invention provides further applications of the banana transporter MhPDR1 or MhPDR2 genes, characterized in that the over-expression of the genes in a plant can promote rapid growth of the plant. In addition, the present invention provides a transgenic plant or partial organ, tissue or cells thereof containing the genes or derivatives thereof; as well as provides further a method for promoting rapid growth of a plant.

6 Claims, 17 Drawing Sheets transgenic strain
Nt-MhPDR1    the control group transgenic strain
Nt-MhPDR2    the control group

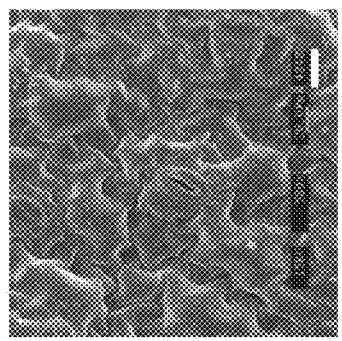
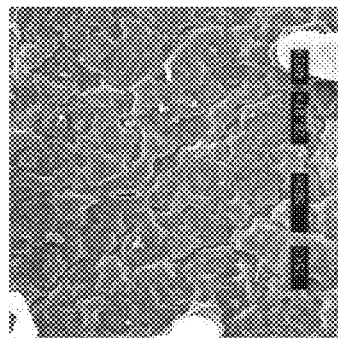
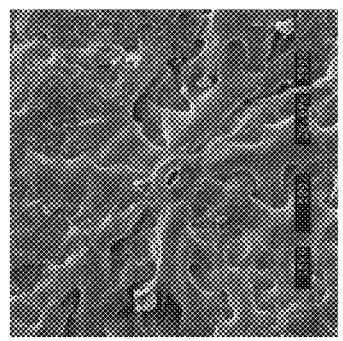
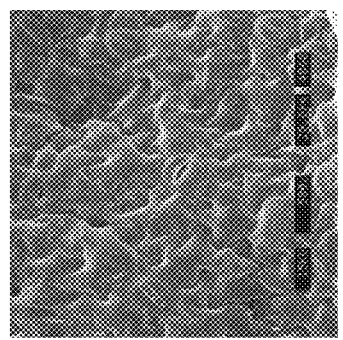
FIG.9A FIG.9B FIG.9C FIG.9D FIG.9E FIG.9F FIG.9G FIG.9H

GENES FOR PROMOTING PLANT GROWTH AND USE THEREOF

BACKGROUND OF THE INVENTION

1. Field of the Invention

The invention relates to genes useful for promoting plant growth, and to the novel use thereof.

2. Description of the Prior Art

Banana (*Musa* spp.) is a monocotyledon crop of Musaceae, one of the important economic fruit plants, and its growing process is susceptible to physiological stress environment so as to affect its quality, and lower profit of farmer. In view of this, in order to increase the production of banana, the inventor devoted to improve the yield of banana by way of gene transfer so that the improved banana possesses better growing potential, its production period can be shortened, as well as its ability to resist stress environment can be enhanced. ATP-Binding Cassette transporter is a membrane protein commonly exists in organisms. It can hydrolyze ATP to perform active transportation of various substances through biological membrane, such as alkaloids, amino acids, heavy metal chelates, inorganic ion, lipid, peptide and sugars (Higgins, 1992; Biemans-Oldehinkel et al., 2006). Among mammal animals and microorganisms, this gene family had been studied extensively. In plants, however, it is a new research field. Animal study pointed out that ATP-Binding Cassette transporter may participate in the transportation process of drugs, where cancer cells can remove anti-cancer drug out of cell to generate drug resistance. Result in microorganism study indicated that ATP-Binding Cassette transporter was associated with the drug resistance of microorganism. While in plants, ATP-Binding Cassette transporter participated in the transportation process of many substances, and played important role in the mechanisms of growth, development, stress environment resistance and disease resistance of plants (Schulz and Kolukisaoglu, 2006). In this invention, gene transfers of banana ATP-Binding Cassette transporters MhPDR1 (*Musa* spp. pleiotropic drug resistance 1) and MhPDR2 (*Musa* spp. pleiotropic drug resistance 2) in a tobacco model plant are utilized as the material, to demonstrate that these genes possess the effect of promoting rapid growth of a plant.

In view of the importance of developing a transferring gene capable of promoting rapid growth of a plant and increasing crop production in the biotechnological industry, the inventor successfully developed genes for promoting rapid growth of plant and uses thereof according to the invention.

SUMMARY OF THE INVENTION

One object of the invention is to provide genes for promoting rapid growth of a plant, characterized in that said genes are selected from banana ATP-Binding Cassette transporter, and promotes the rapid growth of a plant by means of mass expression of said genes.

Another object of the invention is to provide the application of said genes for promoting rapid growth of a plant, characterized in that banana ATP-Binding Cassette transporter gene is transferred in a recombinant plasmid to produce plant cell, organ or transgenic strain containing said recombinant plasmid for application.

Yet another object of the invention is provide a method for promoting rapid growth of a plant, characterized in that mass expression of a banana transporter gene in a plant is carried out to promote the rapid growth of the plant.

Genes for promoting rapid growth of a plant and application thereof that can achieve the above-described objects comprises:

a gene for promoting rapid growth of a plant, comprising at least one selected from the group consisting of banana ATP-Binding Cassette transporter 1 (Mh-PDR1), and banana ATP-Binding Cassette transporter 2 (Mh-PDR2);

wherein said banana ATP-Binding Cassette transporter 1 (Mh-PDR1) has an amino acid sequence as depicted in SEQ ID No: 1 and a nucleotide sequence as depicted in SEQ ID No: 2, and wherein said amino acid sequence in said SEQ ID No: 1 is encoded by the nucleotide sequence in SEQ ID No: 2;

wherein said banana ATP-Binding Cassette transporter 2 (Mh-PDR2) has an amino acid sequence as depicted in SEQ ID No: 3 and a nucleotide sequence as depicted in SEQ ID No: 4, and wherein said amino acid sequence in SEQ ID No: 3 is encoded by the nucleotide sequence in SEQ ID No: 4;

wherein the above-described amino acid sequences include, but not limited to those sequences obtained by mutation, deletion, insertion, or replacement of one to a plurality of amino acid to the sequences depicted in SEQ ID No: 1 or SEQ ID No: 3, while possess the activities of banana ATP-Binding Cassette transporter 1 (Mh-PDR1) or banana ATP-Binding Cassette transporter 2 (Mh-PDR2), as well as the activity of promoting rapid growth of a plant;

wherein the above-described nucleotide sequences include, but not limited to those sequences obtained by mutation, deletion, insertion, or replacement of one to a plurality of nucleotide to the sequences depicted in SEQ ID No: 2 or SEQ ID No: 4, while possess the activity of encoding banana ATP-Binding Cassette transporter 1 (Mh-PDR1) or banana ATP-Binding Cassette transporter 2 (Mh-PDR2), as well as the activity of promoting the rapid growth of a plant.

Term "promoting the rapid growth of a plant" means the nutritive growth, reproductive growth or significantly rapid proliferation, acceleration or increase in the number of cells of a plant.

The above-described term "promoting the rapid growth of a plant" can be further defined as: compared with plant that has not been transferred with the gene described in the invention, the nutritive growth of plant that has been transferred with the gene described in the invention comprises, but not limited to, significant increase on factors such as its root length, plant height, leaf width, while its reproductive growth comprises, but not limited to, factors such as advancing of its blooming time, with its cell number increased significantly also.

In addition to provide gene for promoting rapid growth of a plant, the invention provides further novel application of said gene, includes:

a recombinant plasmid, characterized in that those obtained by constructing banana ATP-Binding Cassette transporter 1 (Mh-PDR1), or banana ATP-Binding Cassette transporter 2 (Mh-PDR2) polynucleotide having open reading frame on the 3' end of promoter of a vector; wherein said polynucleotide is linked to the 3' end of said promoter, said promoter can initiate the transcription of said polynucleotide in an organism containing said recombinant plasmid to over-express mRNA of said polynucleotide, and to over-express the protein of said polynucleotide through translation;

wherein the above-described recombinant plasmid or vector comprises, but not limited to: pBI121 (ClonTech), pCAMBIA1301, pCAMBIA1305 (CAMBIA), or other recombinant plasmid or vector suitable to the invention.

Wherein said promoter includes, but not limited to, Cauliflower mosaic virus (CaMV) 35S promoter, or other promoter suitable to the invention.

According to present invention, it can be over-expressing the above-described genes for promoting plant growth individually and singly in a plant, or over-expressing said genes simultaneously in plants.

In addition to provide the above-described gene for promoting rapid growth of a plant, or derivatives thereof, the invention further provides a method for transferring said genes in a plant (banana), and a way for obtaining therefore, but not to limit the obtaining method or source of the invention; the above-described sequences can be obtained by way of chemical or artificial synthesis.

Term "derivative" used therein means various products or combinations containing the above-described genes for promoting the rapid growth of a plant, such as its protein, recombinant plasmid, recombinant protein, pharmaceutical composition, transgenic cell, as well as transgenic plant, or part of organ or tissue of said transgenic plant containing said genes.

The invention provides further a method for promoting the rapid growth of a plant, comprising the following steps:
step 1: providing cell or tissue of a target plant;
step 2: transferring the above-described recombinant plasmid containing genes for promoting the rapid growth of a plant into the cell or tissue of the target plant provided in said step 1 to obtain a transgenic plant cell or a transgenic plant tissue; and
step 3: cultivating said transgenic plant cell or transgenic plant tissue obtained in step 2 to produce a transgenic plant or part of organ, tissue or cell of said transgenic plant containing the above-described recombinant plasmid;
wherein said transferring procedure described in step 2 includes *Agrobacterium* mediation, genetic recombinant virus infection, transposon vector transferring, gene gun transferring, electroporation, microinjection, pollen tube pathway, liposome mediation, ultrasonic mediation, silicon carbide fiber-mediated transformation, electrophoresis, laser microbeam, polyethylene glycol (PEG), calcium phosphate transferring, or DEAE-dextran-mediated transformation. These features and advantages of the present invention will be fully understood and appreciated from the following detailed description of the accompanying Drawings.

These features and advantages of the present invention will be fully understood and appreciated from the following detailed description of the accompanying Drawings.

BRIEF DESCRIPTION OF THE DRAWINGS

FIG. 1 is a schematic view showing the construction of over-expressed plasmid containing gene for promoting the rapid growth of a plant.

FIG. 2 shows the flow chart for constructing over-expressed plasmid containing gene for promoting the rapid growth of a plant.

FIG. 3 shows the Southern hybridization analytical result of the over-expression of the gene for promoting the rapid growth of a plant in a tobacco transgenic strain.

FIG. 4 shows the reverse transcription polymerase chain reaction analysis in a tobacco transgenic strain for over-expression of the gene for promoting the rapid growth of a plant; the control group is a non-transferred strain;

FIG. 5 shows the root length difference of four-week old seedlings of tobacco transgenic strain with over-expressed vector containing gene for promoting the rapid growth of a plant; the control group is non-transferred strain.

FIG. 6 shows external morphologies of over-expressed tobacco transgenic strain Nt-MhPDR1 and Nt-MhPDR2 with vector containing gene for promoting the rapid growth of a plant; the control group is a non-transferred strain.

FIG. 7 shows the growth survey of over-expressed tobacco transgenic strain with vector containing gene for promoting the rapid growth of a plant; the control group is a non-transferred strain.

FIG. 8 shows the advancing of blooming of over-expressed tobacco transgenic strain with vector containing gene for promoting the rapid growth of a plant.

FIG. 9 shows the observation result of gas hole in over-expressed tobacco transgenic strain with vector containing gene for promoting the rapid growth of a plant; FIG. 9A: non-transferred strain (the control group); FIG. 9B is the Nt-MhPDR1-1 transgenic strain; FIG. 9C is the Nt-MhPDR2-1 transgenic strain; FIG. 9D is the Nt-MhPDR2-2 transgenic strain; FIG. 9E is the Nt-MhPDR2-3 transgenic strain; FIG. 9F is the Nt-MhPDR2-4 transgenic strain; FIG. 9G is the Nt-MhPDR2-5 transgenic strain; FIG. 9H is the Nt-MhPDR2-6ransgenic strain; Bar=20 μm;

DETAILED DESCRIPTION OF THE PREFERRED EMBODIMENT

Figure 1A:
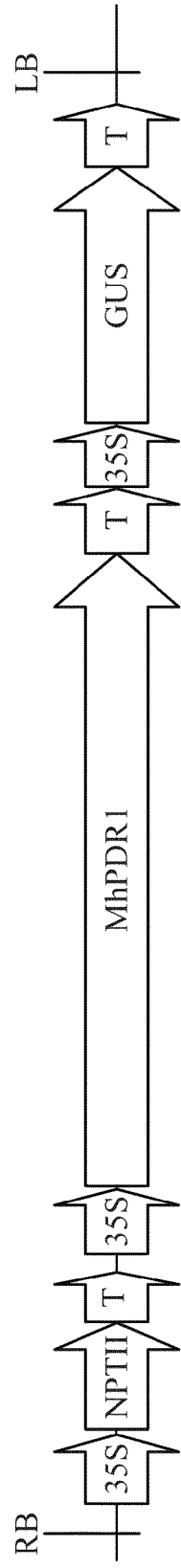
FIG. 1A shows the schematic view for constructing MhPDR1.

The invention will be illustrated in more details with the following examples; however, the invention is not limited by those examples.

Example 1

The Transfer of Banana ATP-Binding Cassette Transporter Genes for Promoting Rapid Growth of a Plant 1. Source of Banana λEMBL3 Genomic Library Banana genomic library was obtained by extracting genomic DNA of a banana variety, Hsien Jin Chiao, *Musa* spp., AAA group, plant leave, and then, by using bacteriophage λEMBL3 as the vector, genomic library was constructed by means of cleavage replacement of DNA fragment.

2. Preparation and Labeling of Nucleic Acid Probe

A gene fragment of *Arabidopsis thaliana* ecotype Columbia ETR1 gene (GeneBank accession number NP_176808) was used as the template to carry out the preparation of a nucleic acid probe by using Prime-A-Gene kit (Promega, USA) according to the following process: total reaction volume was 50 μL, comprising: 1× labeling buffer, pH6.6 {50 Mm Tris-HCL, pH8.3, 5 mM $MgCl_2$, 2 mM DTT, 0.2M HEPES [N-(2-hydroxyethyl)piperazine-N'-(2-ethanesulfonic acid)], $26A_{260}$ unit/mL random hexadeoxyribonicleotides}, 20 μM dATP, dGTP, dTTP, 500 ng/mL denatured DNA template, 400 μg/mL Bovine serum albumin (BSA), 50μ Ci [$\alpha$-$^{32}$P] dCTP (333 nM), and 5 unit Klenow DNA Polymerase. After reacting at 37° C. for 2 hours, 2 μL 0.5M EDTA (pH 8.0) was added to terminate the reaction, followed by adding 8 μL tracing dye (50% glycerol, 0.25% bromophenol blue), and then the reaction solution was passed through Sephadex-G50 chromatograph column, eluted with TE (pH7.6) buffer solution, every 160~180 μL was collected in a tube, and after determining radioactivity of every tube in a liquid scintillation counter (Liquid Scintillation Counter, Beckman 1801), suitable amount of eluate with highest radioactivity was used as the probe.

3. Genomic Library Screening of Banana ATP-Binding Cassette Transporter Gene Mh-PDR Banana genomic library was screened by plaque hybridization. At first, *E. coli* strain XL1-Blue MRA (P2) was used as the infection host of λEMBL3, and was cultured in a NZY medium (every liter containing 5 g NaCl, 2 g $MgSO_4.7H_2O$, 5 g yeast extract), and total of 150 million plaque forming units were screened under high stringency.

A nitrocellulose membrane was used to transfer bacteriophage. The transfer membrane was treated with denature buffer (0.5M NaOH, 1.5M NaCl) for 2 minutes, then treated with neutralization buffer [0.5M Tris base, 1.5M NaCl, 0.035% HCl (v/v)] for 5 minutes, and finally, immersed in a 2×SSPE (1×SSPE 0.18M NaCl, 10 mM $NaH_2PO_4$, 1 mM EDTA pH7.4) for 30 seconds. Thereafter, it was treated in an 80° C. vacuum oven for 2 hours to fix the bacteriophage DNA. Then, it was placed in a solution containing 2×SSPE and 0.1% SDS, and was shaken mildly at room temperature for one hour. Then, placed the nitrocellulose membrane in a pre-hybridization solution containing 5×SSPE, 5×BFP (1×BFP containing 0.02% BSA, 0.02% Ficoll-400000, 0.02% PVP-360000), 0.1% SDS, 50% formamide and 500 μg/mL salmon sperm DNA, and carried out pre-hybridization reaction at 37° C. for 2 hours. Thereafter, the radio-labeled probe was used to carry out hybridization reaction in 5×SSPE, 1×BFP, 0.1% SDS, 50% formamide and 100 μg/mL salmon sperm DNA with the membrane at 37° C. for 16~18 hours. Then, the nitrocellulose membrane was treated with wash buffer I (5×SSPE, 0.1% SDS) twice at room temperature for 15 minutes, as well as twice with wash buffer II (1×SSPE, 0.5% SDS) at 37° C. for 15 minutes to wash off non-specific probe. After developed by press exposure with X-ray film at −80° C. (Kodak XAR film), the bacteriophage containing target gene DNA could be detected. Said bacteriophage was isolated from the medium, kept in a SM buffer solution containing 0.03% chloroform, and was purified several times to obtain genomic clone of banana ATP-Binding Cassette transporter.

4. Extraction of Selected Bacteriophage Clone DNA

The bacteriophage liquor of the target clone was cut open with toothpick in a NZY solid medium, 3 mL Top agar containing host cell of *E. coli* XL1-Blue MRA (P2) was added, and was cultivated in the NZY solid medium at 37° C. for 8 hours. On the next day, a capillary was used to poke up single plaque agar piece on the cut line, and was cultured by spreading over a NZY solid medium at 37° C. for 7~11 hours. Then the medium was placed in a 4° C. refrigerator, SM buffer (each liter containing 5.8 g NaCl, 2 g $MgSO_4.7H_2O$, 50 ml 1 M Tris-HCl (pH 7.5), 0.1 g gelatin) was added to dissolve off the bacteriophage. The solution was collected in a centrifuge tube, chloroform was added to 0.03%, and was centrifuged at 4° C. and 7,000 rpm (Beckman J2-MC, JS-13.1) for 5 minutes, and was kept at 4° C. for use later. Thereafter, the above-described mass reproduced target clone bacteriophage was used to infect host cells at a cell count ratio of 5:1. after mixed with 1 mL SM buffer solution and 2.5 mM $CaCl_2$ 5 mL, the solution was stood still at room temperature for 15 minutes, and then at 37° C. for 45 minutes. Thereafter, 100 mL 2×NZY liquid medium (0.4% $MgSO_4.7H_2O$, 2% NaCl, 1% bacto-yeast extract, 2% NZ amine, 0.2% casamino acid, 5 mM $MgSO_4$, 25 mM Tris-HCl pH7.5) was poured in and was cultured by shaking at 37° C. and 240 rpm for more than 8 hours. 4.5 mL Chloroform was then added and treated by shaking at 37° C. and 240 rpm for 15 minutes. The suspension was then centrifuged at 4° C. and 7,000 rpm for 20 minutes (Beckman J2-MC, JA 10 rotor). To the supernatant, 100 μL DNase I (1 mg/mL) and 100 μL RNaseA (10 mg/mL) was added and treated at 37° C. and 80 rpm for 45 minutes. Then, 33 mL 4M NaCl was added and was treated in an ice bath for 1 hour. Thereafter, 33 mL ice-cold 50% polyethylene glycol was added, and precipitated at 4° C. overnight. The suspension was centrifuged at 4° C. and 5,000 rpm for 20 minutes (Beckman J2-MC, JA 10 rotor). The supernatant was removed, and the residue was air dried. 500 μL PKB solution (10 mM NaCl, 10 mM Tris-HCl pH8.0, 10 mM EDTA, 0.1% SDS) was added to re-suspend the precipitate. Then, proteinase K (final concentration: 12.5 μg/mL) was added and reacted at 37° C. for 20 minutes. This was extracted in turn with equal volume of phenol, PCI (phenol:chloroform: isoamyl alcohol=25:24:1), and CI (chloroform:isoamyl alcohol=24:1). After centrifuged at room temperature and 14,000 rpm for 5 minutes, 2-fold volume of −20° C. 100% ethanol was added to the supernatant, and centrifuged at 4° C. and 14,000 rpm for 10 minutes. The supernatant was decanted, and the residue was air dried. The precipitated DNA was washed with 70% ethanol and 100% ethanol, respectively. It was dissolved in TE buffer solution (pH7.5) and stored at 4° C. for later use.

5. Sequencing of DNA

An automatic nucleic acid sequencer (ABI sequencer 377) was used to carry out the sequencing of DNA to obtain sequences of Mh-PDR genomic clone of banana ATP-Binding Cassette transporter gene.

6. Establishment of Complementary DNA Library (cDNA Library)

Total banana RNA was extracted at first as followed: plant material was cut and was ground in liquid nitrogen into powder. 20 mL 65° C. Extraction buffer (2 M NaCl, 25 mM EDTA, pH 8.0, 100 mM Tris-HCl, spermidine 0.5 g/L, 3% Hexadecyl trimethyl-ammonium bromide, 3% polxviuyl-pyrrolidone-40, 0.4% 2-mercaptoethanol) was added, stirred in a homogenizer, and treated at 65° C. for 10 minutes. Equal amount of CI (chloroform:isoamyl alcohol=49:1) was added, mixed and centrifuged. The supernatant was re-extracted once more, and ⅓-fold volume of 8 M LiCl was added thereto. After precipitated at 4° C. overnight, it was centrifuged at 4° C. The supernatant was discarded, and the RNA residue was suspended in 0.5% SDS. Equal volume of CI was added and mixed by shaking for several seconds. After centrifuged at 4° C., 2-fold volume of 100% ethanol was added into the supernatant, and the mixture was precipitated at −20° C. Thereafter, it was centrifuged at 4° C. to discard the supernatant. 500 μL of 70% ethanol was added, centrifuged at 4° C. to discard the supernatant. Then, 500 μL of 100% ethanol was added, centrifuged at 4° C. to discard the supernatant. The RNA precipitate was air dried. The RNA was then dissolved in a suitable amount of DEPC water, the concentration was determined and then stored for later use. Finally, complementary DNA library was completed by using λZAP cDNA synthesis kit provided by Stratagene.

7. Screening of Complementary DNA Library

In order to obtain the cDNA sequence of banana ATP-Binding Cassette transporter gene, a fragment of the genomic clone was used as the probe, plaque hybridization was used to screen cDNA library of *Musa* spp. Hsien Jin Chiao, AAA group, and obtained two type of ATP-Binding Cassette transporter cDNA clone. Of these, pMaABC-29 cDNA had a nucleotide length of 4731 bp (SEQ ID No: 2), which could translate a protein having a total length of 1452 amino acids (SEQ ID No: 1), a pre-estimated molecular weight of 163 kDa, an isoelectric point of 8.20. Its corresponding gene was named as Mh-PDR1; and clone pMaABC-74p cDNA had a nucleotide length of 4760 bp (SEQ ID No: 4), could translate a protein having a total length of 1468 amino acids (SEQ ID No: 3), a pre-estimated molecular weight of 165 kDa, and isoelectric point of 8.50. Its corresponding gene was named as Mh-PDR2. The identity of the amino acid sequence between these two clones was 85.3%.

Example 2

Figure 1B:
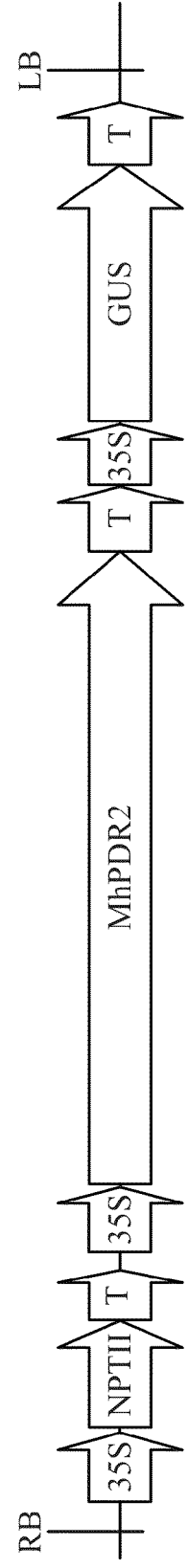
FIG. 1B shows the schematic view for constructing MhPDR2.

Construction of Vector Containing Gene for Promoting the Rapid Growth of a Plant and its Gene Transfer Vector containing gene for promoting the rapid growth of a plant was carried out as described in FIG. 1 under a flow scheme as followed:

(1) Material for Plasmid a. pRT99gus plasmid, having a total length of 6.7 Kb, containing a GUS reporter gene under control of CaMV 35S promoter, and a NOS terminator (GenBank accession no. L09137).

b. pGKU plasmid, having a total length of 7.4 Kb, containing a NPTII plant screening gene under control of CaMV 35S promoter, a GUS reporter gene under control of CaMV 35S promoter and a NOS terminator.

(2) Construction Flow Scheme

Figure 2A:
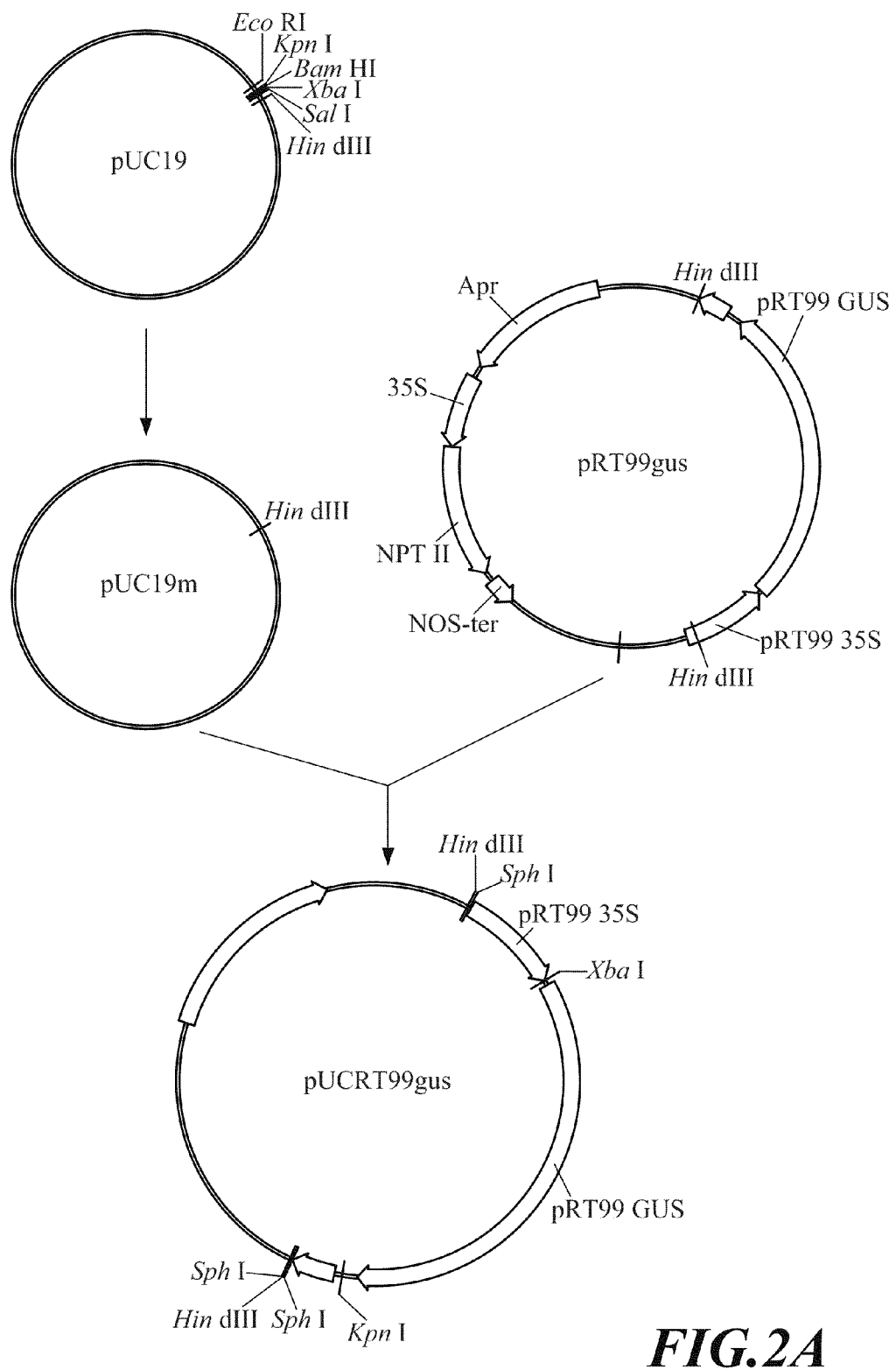
FIG. 2A: the construction of plasmid pUCRT99gus.

Step 1: Construction Strategy of pUCRT99gus pUC19 was cleaved at first with EcoRI and SalI to remove large part of MCS region on the pUC19, the then blunt treated with Klenow enzyme, and subjected to electrophoresis separation to recover a 2.6 kb fragment. This fragment was subjected to self-ligation to obtain an intermediate vector pUC19m. This intermediate vector pUC19m was cleaved with restriction enzyme HindIII to recover a fragment of about 2.6 kb in length. A plasmid pRT99gus was cleaved completely with HindIII to recover a DNA fragment of 2.6 Kb that was used as the DNA fragment to be inserted. These two fragments were subjected to ligation to obtain a plasmid having total length of 5.2 Kb, which was named as pUCRT99gus (FIG. 2A).

Step 2: Construction Strategy of Plasmid pMhPDR1

Banana total RNA treated with DNase was subjected to reaction by using One-Step RT-PCR Kit (GeneMark), wherein the reaction solution contained, 0.1 μg/μL template RNA, 50 ng/μL primers, 1× Reaction Mix, 1× Enhancer, 2% Enzyme Mix. The reaction temperature was 50° C. 30 minutes, 94° C. 2 minutes, then 35 cycles of 94° C. 30 seconds, 59° C. 30 seconds, and 72° C. 1 minute. Finally, reacted at 72° C. for 10 minutes, stored at 4° C. for later use. Primers used included:

```
forward primer PDR1-1:
(contained XbaI restriction site, total 27 mer)
5'-tcc tctagaatggaaccgagcgaggtg-3'      (SEQ ID No: 5)
        XbaI Met reverse primer PDR1-2:
(contained KpnI restriction site, total 28 mer)
5'-agc ggtacctcatctcttctggaagttg-3'     (SEQ ID No: 6)
        KpnI
```

Figure 2B:
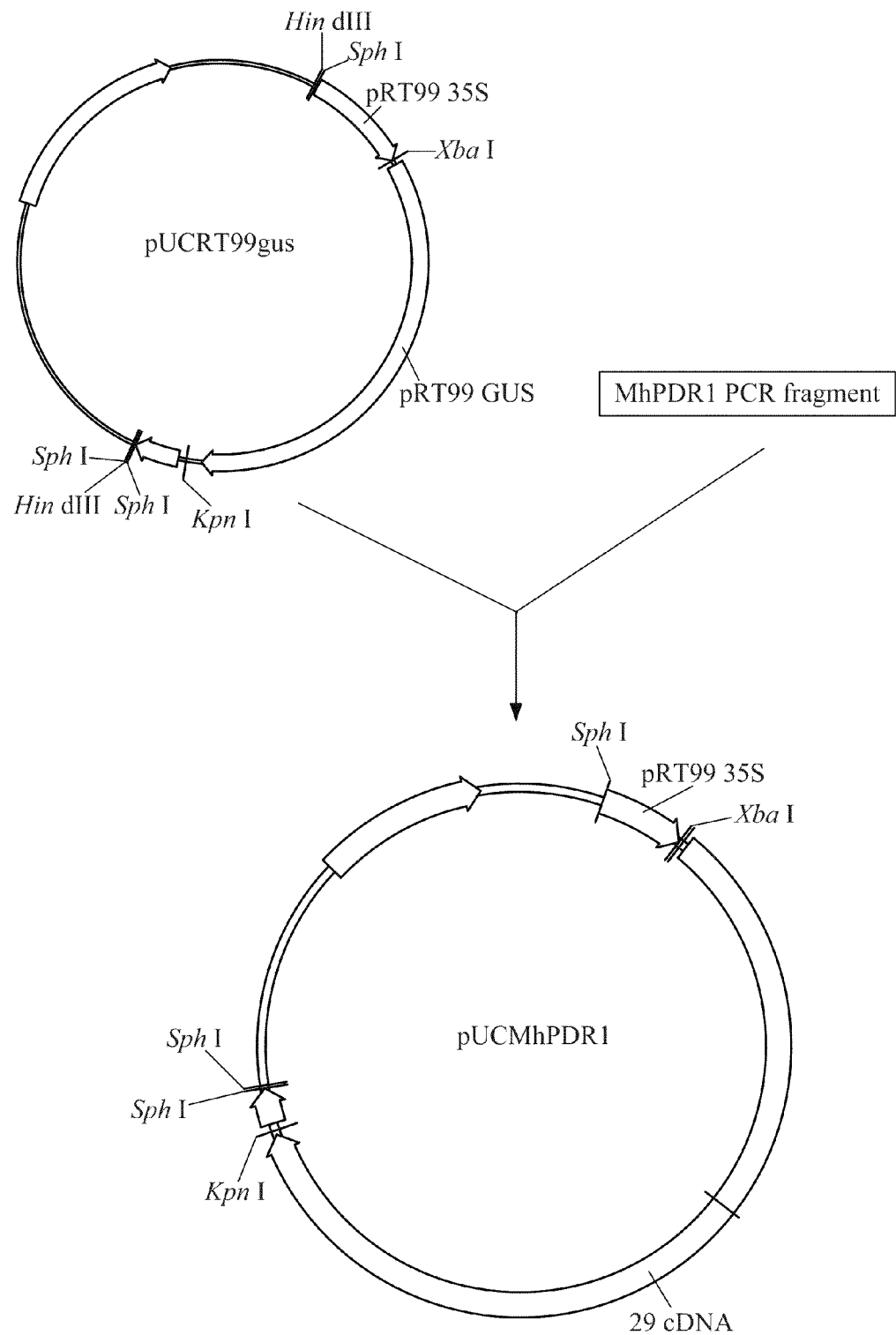
FIG. 2B: the construction of plasmid pUCMhPDR1.
Figure 2C:
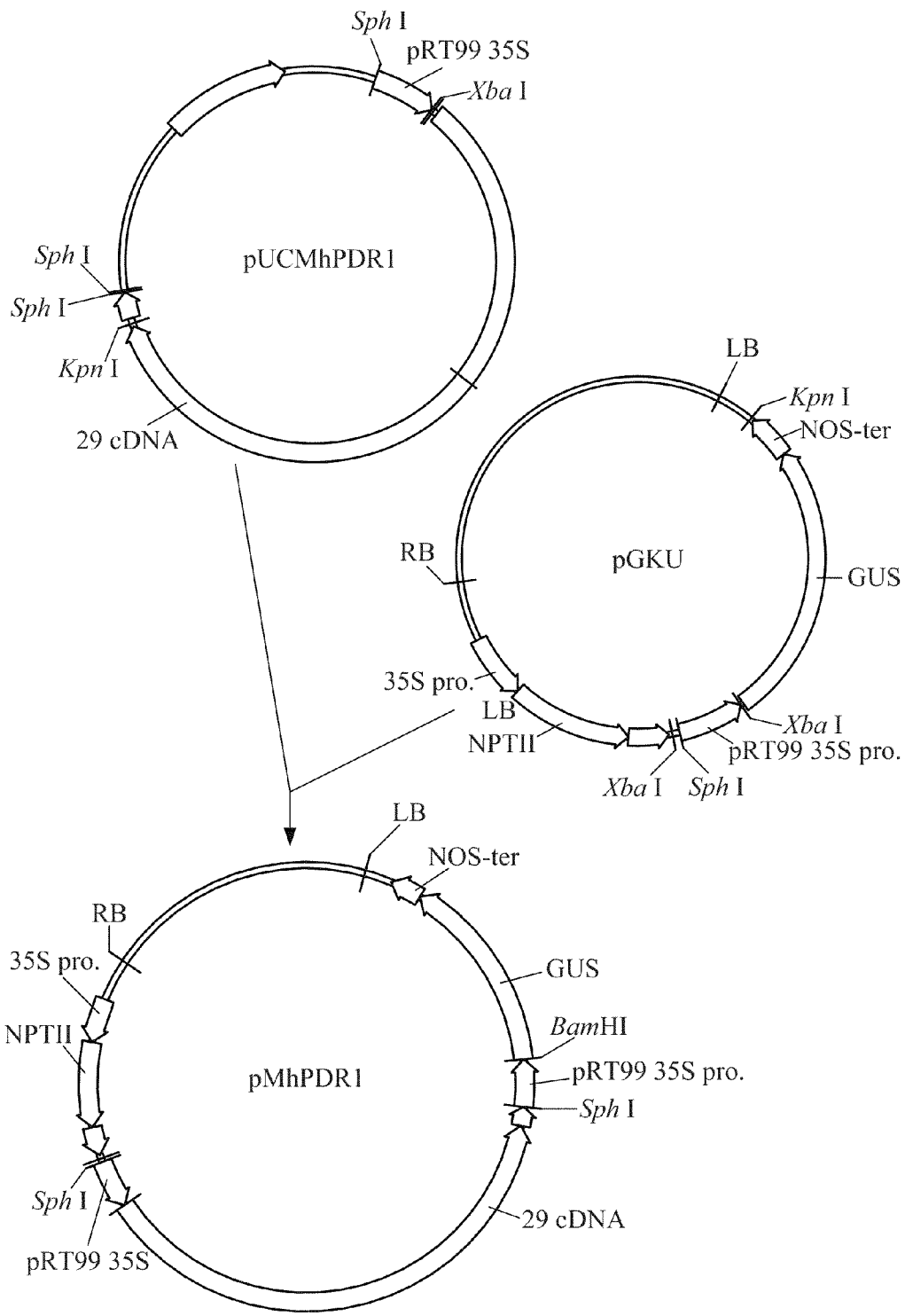
FIG. 2C: the construction of plasmid pMhPDR1.

Gene fragments obtained in the above-described reverse transcription polymerase chain reaction were cleaved completely with XbaI and KpnI to recover a DNA fragment of 4.8 Kb, which was used as the DNA fragment to be inserted. pUCRT99gus plasmid was cleaved completely with XbaI and KpnI to recover a DNA fragment of 3.4 Kb, which was used as the vector DNA fragment. These two fragments were subjected to ligation to obtain a plasmid having a total length of about 8.2 Kb, which was named as pUCMhPDR1 (FIG. 2B). Plasmid pUCMhPDR1 was cleaved completely with SphI to recover a DNA fragment of 5.3 Kb, which was used as the DNA fragment to be inserted. Plasmid pGKU was cleaved completely with SphI to recover a DNA fragment of 7.4 Kb, which was used as a vector DNA fragment. These two fragments were subjected to ligation to obtain a plasmid having a total length of 12.89 Kb, which was named as pMhPDR1 (FIG. 2C).

Step 3: Construction Strategy of Plasmid pMhPDR2

Figure 2D:
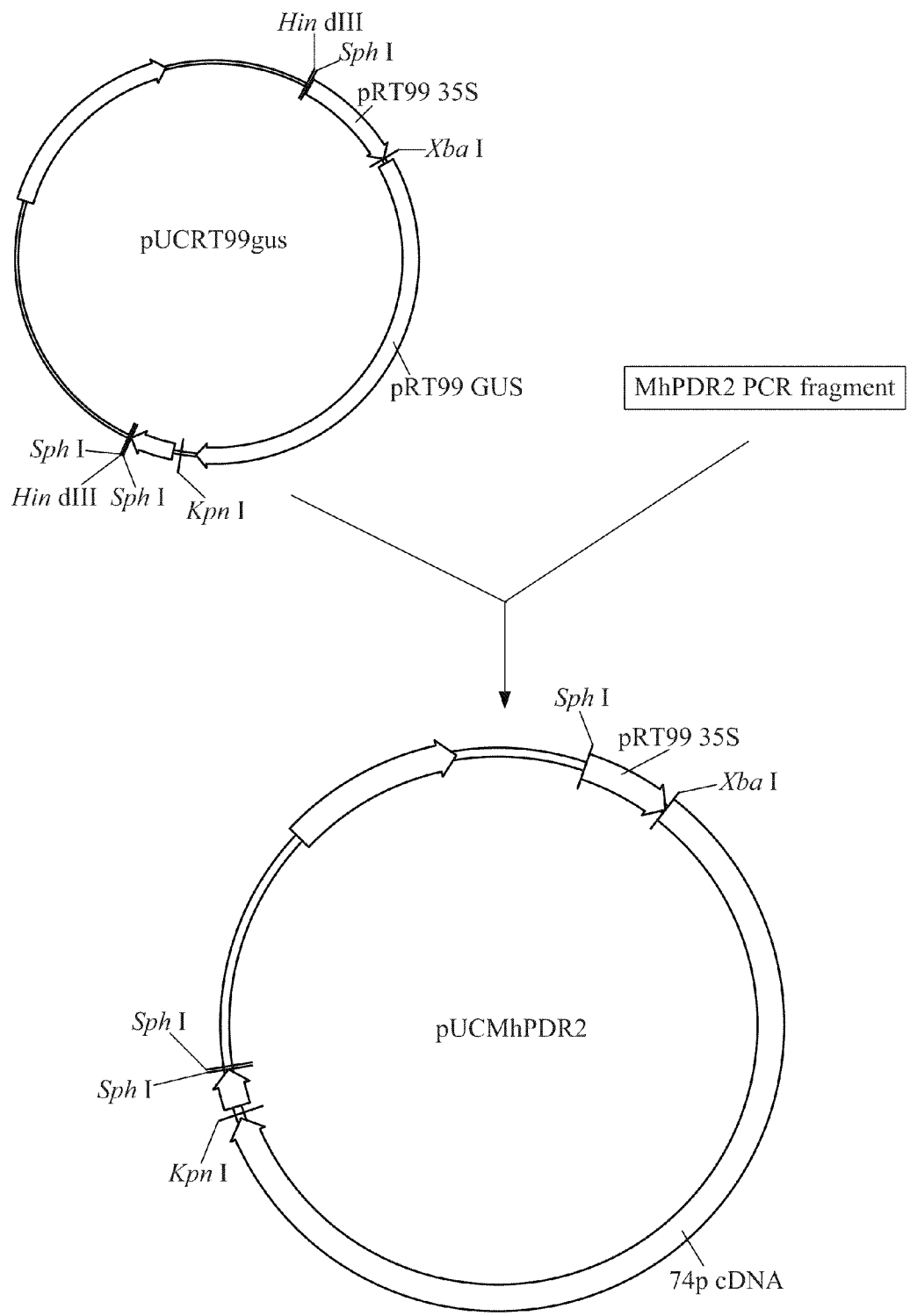
FIG. 2D: the construction of plasmid pUCMhPDR2.
Figure 2E:
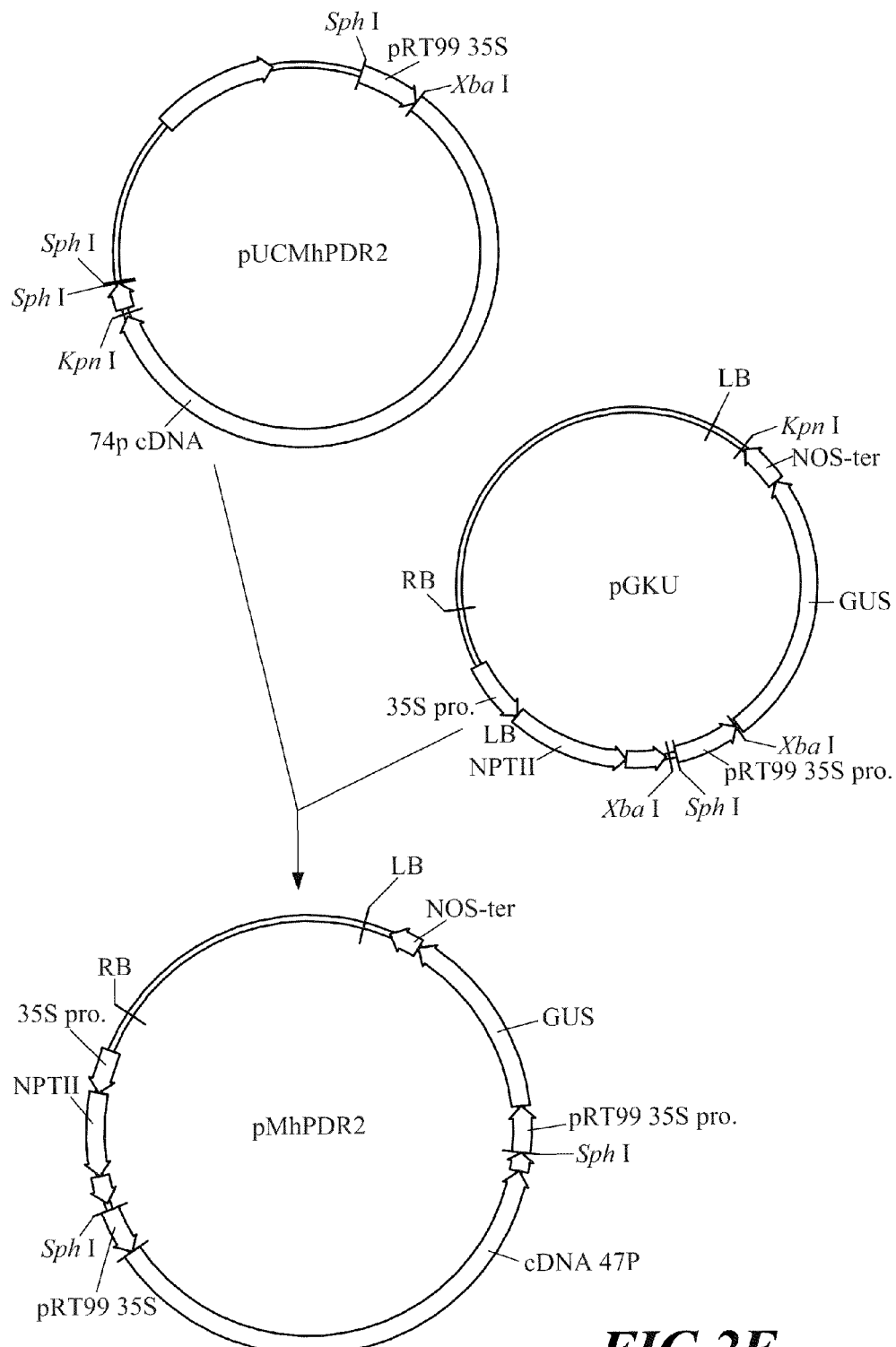
FIG. 2E: the construction of plasmid pMhPDR2.

Banana total RNA treated with DNase was subjected to reaction by using One-Step RT-PCR Kit (GeneMark), wherein the reaction solution contained, 0.1 μg/μL template RNA, 50 ng/μL primers, 1× Reaction Mix, 1× Enhancer, 2% Enzyme Mix. The reaction temperature was 50° C. 30 minutes, 94° C. 2 minutes, then 35 cycles of 94° C. 30 seconds, 59° C. 30 seconds, and 72° C. 1 minute. Finally, reacted at 72° C. for 10 minutes, stored at 4° C. for later use. Primers used included:

forward primer PDR2-1:
(contained XbaI restriction site, total 27 mer)
5'-tcc tctagaatggagccgagcgaggtg-3' (SEQ ID No: 7)
       XbaI Met reverse primer PDR2-2:
(contained KpnI restriction site, total 28 mer)
5'-agc ggtacctcatctcttttggaagttg-3' (SEQ ID No: 8)
       KpnI Gene fragments obtained in the above-described reverse transcription polymerase chain reaction were cleaved completely with XbaI and KpnI to recover a DNA fragment of 4.7 Kb, which was used as a DNA fragment to be inserted. Plasmid pUCRT99gus was cleaved completely with XbaI and KpnI to recover a DNA fragment of 3.4 Kb, which was used as a vector DNA fragment. These two fragments were subjected to ligation to obtain a plasmid having a total length of about 8.1 Kb, which was named as pUCMhPDR2 (FIG. 2D). Plasmid pUCMhPDR2 was cleaved completely with SphI to recover a DNA fragment of 5.3 Kb, which was used a DNA fragment to be inserted. Plasmid pGKU was cleaved completely with SphI to recover a DNA fragment of 7.4 Kb, which was used as a vector DNA fragment. These two fragments were subjected to ligation to obtain a plasmid having a total length of about 12.8 Kb, which was named as pMhPDR2 (FIG. 2E).

2. *Agrobacterium* Transformation by Electroporation

*Agrobacterium* cell to be transformed was thawed on ice, 100 ng plasmid DNA was mixed well thereto on an ice-water bath, and placed in an electroporation cuvette. After electric shock in an Electro Cell Manipulator 200 (BTX®) with a voltage of 1420 V, 0.5 mL YEB liquid medium was added, cultured at 28° C. for 1 hour, then placed in a solid medium containing suitable antibiotics, and cultured at 28° C. for 48 hours.

3. *Agrobacterium* Mediated Gene Transfer

A single colony of *Agrobacterium* with vector construct containing gene for promoting the rapid growth of a plant in 20 mL YEB liquid medium containing antibiotics (each liter containing 5 g Beef extract, Yeast 1 g extract, 5 g Peptone, 5 g Mannitol, 0.5 g $MgSO_4$), and cultured by shaking at 28° C. and 240 rpm for 48 hours. The bacteria liquor was diluted to $OD_{600}=0.8$. 20 mL bacteria liquor was placed in a glass Petri dish. A tobacco leaf was cut in the bacteria liquor into round leaf piece of 1.5 cm×1.5 cm, which round leaf pieces were placed on N01B1 solid medium [MS, 0.1 mg/L 1-naphthyl acetic acid, 1 mg/L BA, 3% sucrose, pH5.7, 0.7% agar], and cultured at 25° C., 16 hour-lighting environment for 3 days. These round leaf pieces were then placed on a N01B1 solid medium containing 250 mg/L cefotaxime and 100 mg/L kanamycin, and screened by culturing at 25° C. and 16-hour lighting environment for about two weeks. Those round leaf pieces with grown shoot were placed on N01B1 solid medium containing 250 mg/L cefotaxime and 200 mg/L kanamycin, and sub-screened by cultured at 25° C. and 16-hour lighting environment. Until the shoot had grown to about 1 cm in length, non-whitened shoots could be cut off, cottage on a MS solid medium containing 250 mg/L cefotaxime and 200 mg/L kanamycin, and cultivated at 25° C. and 16-hour lighting environment to develop into a plant.

Example 3

Molecular Assay on Tobacco Transferred with Gene for Promoting the Rapid Growth of a Plant Using Southern Hybridization Assay This example demonstrated the gene integrity after inserting transfer gene into genome of tobacco transgenic strain by using Southern hybridization assay, which comprised of cleaving tobacco transgenic strain with restriction enzymes, using target gene as the probe and carrying out hybridization assay.

1. Extraction of Transgenic Strain Genomic DNA

Leaves of transgenic strain were quick frozen in liquid nitrogen, 1 g of the leave was placed in a mortar and ground into powder. 15 mL extraction buffer (100 mM Tris-HCl, pH 8.0, 50 mM $Na_2EDTA$, pH 8.0, 500 mM NaCl, 100 mM 2-mercaptoethanol) was added thereto and mixed well. 1 mL 20% SDS was then added and stood still at 0° C. for 20 minutes. Next, it was centrifuged at 8,800 rpm and 4° C. for 30 minutes (Beckman J2-MC, JA-18 rotor). The supernatant was filtered through 100 meshes Nylon mesh into 10 mL -20° C. isopropanol contained in a centrifuge tube, and stood still at −20° C. for 30 minutes. Then, centrifuged at 8,800 rpm and 4° C. for 30 minutes to discard the supernatant. 0.7 mL 4° C. High-TE buffer solution (50 mM Tris-HCl, pH 8.0, 50 mM $Na_2EDTA$) was added to the residue to dissolve the product, which was centrifuged at 4° C. and 13,200 rpm for 10 minutes. The supernatant was removed to a new centrifuge tube, 75 µL 3 M sodium acetate (pH 5.2) and 500 µL isopropanol was added thereto. After mixed homogeneously, it was stood still at −20° C. for 30 minutes. Then, it was centrifuged at 13,200 rpm and 4° C. for 30 minutes to discard the supernatant. After salt washed with 70% ethanol and 100% ethanol, 100 µL TE buffer solution (10 mM Tris-HCl, pH 8.0, 1 mM $Na_2EDTA$) and suitable amount of RNaseA were added, and reacted at 37° C. for 30 minutes, stored at 4° C. for later use.

2. Preparation of Nucleic Acid Probe and Southern Hybridization Analysis

The synthesis and labeling of probe was carried out by using Primer-a-gene kit (Promega). After reacting at 37° C. for 1 hour, 2 µL 0.5M $Na_2EDTA$ was added to terminate the reaction, and 8 µL tracing dye (50% glycerol, 25% bromophenol blue) was added also. The reaction solution was passed through Sephadex-G50 chromatograph column, and the synthetic material was eluted off with TE buffer solution (pH 7.6), which was counted in a liquid scintillation counter (Liquid Scintillation Counter; Beckman 6501) to determine the radioactivity, and several collection tubes of elution solution with highest activity were used as the probe.

20 µg transgenic strain genomic DNA was cleaved with restriction enzyme BamHI, and separated by electrophoresis on 0.7% agarose gel. The gel was soaked successively in 2.5 N HCl, denature buffer solution (1.5 M NaCl, 0.5 M NaOH), and neutralization buffer solution (1.5 M NaCl, 0.5 M Tris-HCl, pH 8.0) each for 15 minutes, and the process was repeated twice. The gel thus-treated was DNA transferred on Hybond N transfer membrane, and cross-linked under condition of UV 120 $mJ/cm^2$ (Spectrolinker XL-1500), which was then placed in a 80° C. vacuum oven for 1 hour to immobilize DNA. Thereafter, the transfer membrane was soaked at first in a pre-hybridization solution (6×SSPE, 1% SDS, 5×BFP, 50 µg/mL salmon sperm DNA) and treated at 65° C. for more than 2 hours. Next, the transfer membrane was soaked in hybridization solution containing the above-described probe (6×SSPE, 0.5% SDS, 5×BFP, 250 µg/mL salmon sperm DNA, 10% dextran sulfate), and treated at 65° C. for 16-18 hours. It was shaken in a wash solution I (2×SSPE, 0.1% SDS) at room temperature for 15 minutes, and this process was repeated twice. Then, it was shaken mildly in a wash solution II (1×SSPE, 0.1% SDS) at 65° C. for 15 minutes, and this process was repeated twice. Finally, it was pressed exposure on a X-ray film at −80° C.

3. The Result of Southern Hybridization Analysis

Figure 3A:
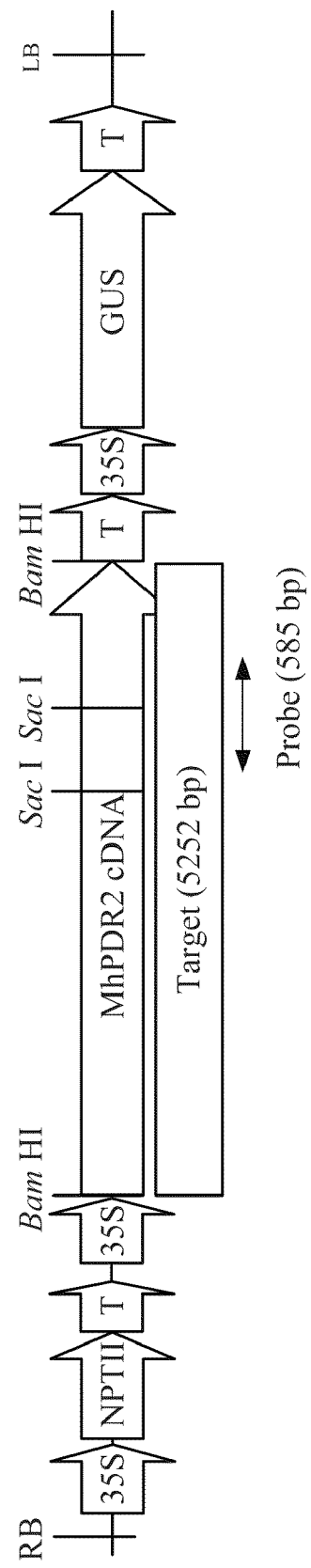
FIG. 3A: construction chart and selection region of probe.
Figure 3B:
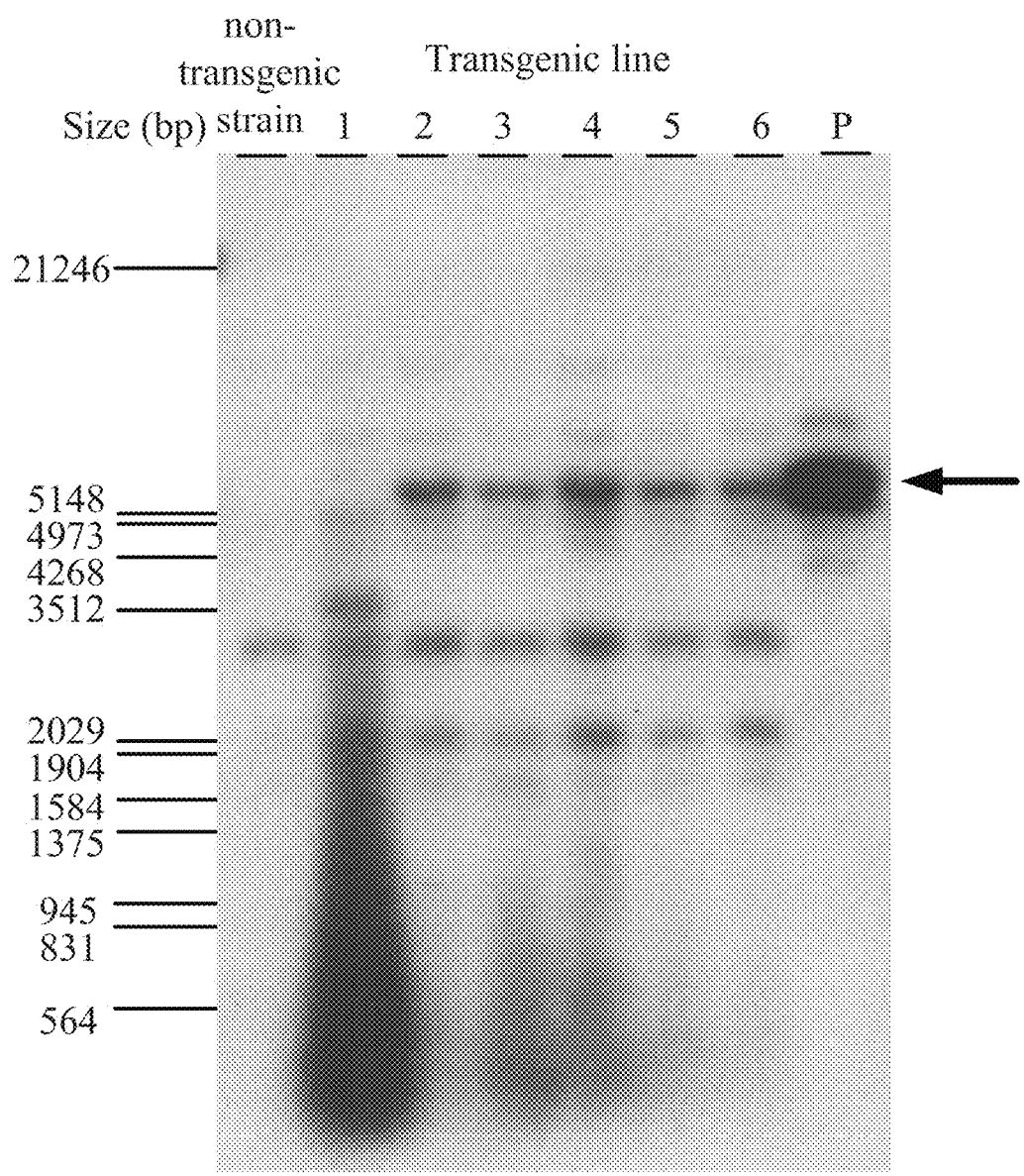
FIG. 3B: Southern hybridization analysis indicating that said gene had been inserted entirely into the transgenic tobacco genome, wherein P stands for a probe.

This example used MhPDR2 as the illustrative example to compare the nucleotide sequence of MhPDR2 decoding region and of the tobacco ATP-Binding Cassette transporter gene, banana MhPDR2 gene had an identity of 68.2% against tobacco NtPDR1 (GenBank accession no. AB075550); and an identity of 67.9% against tobacco NtPDR2 gene (GenBank accession no. AB109389). Therefore, region with low identity was selected as the probe 585 bp used in Southern hybridization analysis (FIG. 3A) to carry out hybridization. The result of hybridization was shown in FIG. 3B. All of transgenic strain Nt-MhPDR2-2~6 yielded hybridization signals at site of the predicted target fragment 5.2 Kb. This demonstrated that said gene for promoting rapid growth had been transferred integrally and successfully in the tobacco genome. In addition, both non-transgenic strain and transgenic strain Nt-MhPDR2-1~6 yielded hybridization signals at 1.4 Kb, 2.4 Kb, 3.0 Kb, 9.0 Kb and 12.0 Kb, which was postulated to be tobacco endogenous homogeneous similar genes.

Example 4

Gene Expression Assay of Tobacco Transferred with Gene for Promoting the Rapid Growth of a Plant This Example assayed the expression of transferred gene in tobacco by using reverse transcription polymerase chain reaction. The results indicated that after transferring gene for promoting the rapid growth of a plant into tobacco, gene expression could be carried out readily, and products of the gene for promoting the rapid growth of a plant could be accumulated.

1. Extraction of Transgenic Strain RNA

Material frozen in liquid nitrogen was ground in a mortar with liquid nitrogen to break the plant tissues. To each gram of the powdered tissue, 2-3 mL solution D without sarcosyl [4 M guanidiun thiocyanate, 25 mM sodium citrate (pH7.0), 0.1 M β-mercaptoethanol], and equal volume of ⊥PCI (phenol:chloroform:isoamyl alcohol=25:24:1) were added and mixed well in a homogenizer. More sarcosyl was added to a final concentration of 0.5%, which, after mixing in a homogenizer, was centrifuged at 4° C. and 10800 rpm for 20 minutes (Beckman J2-MC, JS 13.1). The supernatant was extracted once with equal volume of PCI, and finally, equal volume of CI (chloroform:isoamyl alcohol=49:1) was used to centrifuge extraction of the supernatant. Volume of the supernatant was determined, 1/10 volume of 3 M NaOAc (pH5.2) and 2.5-fold volume of −20° C. 100% ethanol were added, which was shaken homogeneously and precipitated at −80° C. overnight. On the next day, it was centrifuged at 4° C. and 10800 rpm for 15 minutes. The residue was desalted with 2 mL 70% ethanol and 100% ethanol, respectively, under the condition of centrifuging at 4° C. and 10800 rpm for 5 minutes. The supernatant was discarded, and the RNA was dissolved in diethyl pyrocarbonate (DEPC)-treated water. LiCl was added to the final concentration of 2.5 M. Then, 1% β-mercaptoethanol was added and the mixture was precipitated at −80° C. overnight. On the third day, it was centrifuged at 10800 rpm and 4° C. for 90 minutes, desalted with 70% ethanol and 100% ethanol, respectively. The RNA was air dried, dissolved in DEPC water, and determined quantitatively by measuring its $OD_{260}$.

2. Demonstration of Gene Expression by Reverse Transcription Polymerase Chain Reaction Tobacco total RNA treated with DNase was subjected to reaction by using One-Step RT-PCR Kit (GeneMark), wherein the reaction solution contained 0.1 μg/μL template RNA, 50 ng/μL primers, 1× Reaction Mix, 1× Enhancer, 2% Enzyme Mix. The reaction temperature was 50° C. 30 minutes, 94° C. 2 minutes, and then 40 cycles of 94° C. 30 seconds, 57.5° C. 30 seconds, and 72° C. 1 minute. Finally, it was reacted at 72° C. for 10 minutes, and stored at 4° C. for later use. Transgenic strain Nt-MhPDR1 and Nt-MhPDR2 used the following primers:

```
forward primer cABC1: total 16 mer
5'-atggagccgagcgagg-3'                  (SEQ ID No: 9)

reverse primer 74P-F3: total 19 mer
5'-ggcctctagcatgttaagg-3'               (SEQ ID No: 10)
```

Figure 4A:
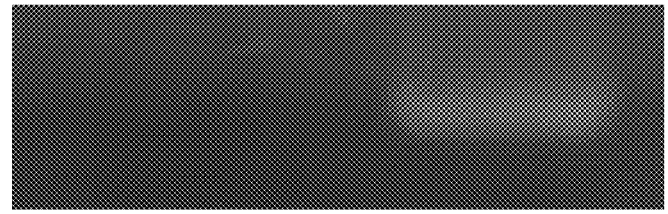
FIG. 4A: the gene expression of Nt-MhPDR1-transferred tobacco.
Figure 4A:
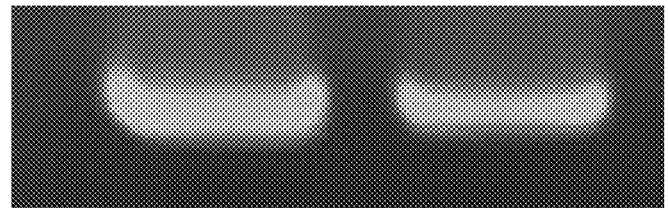
Figure 4B:
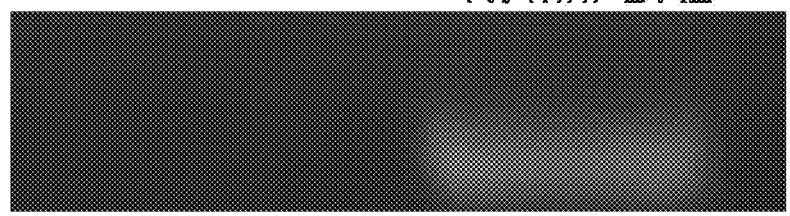
FIG. 4B: the gene expression of Nt-MhPDR2-transferred tobacco; TRPB2 signal is the control group shows the loading amount of RNA, said gene is a tobacco RNA polymerase subunit (RNA polymerase subunit 2) expressed normally.
Figure 4B:
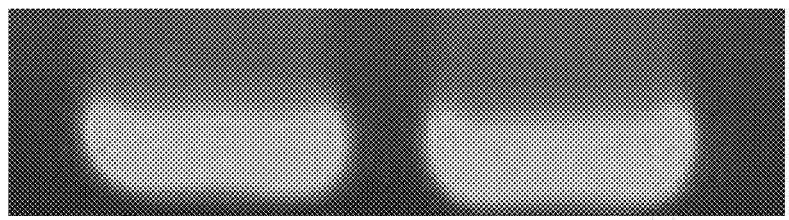
Figure 5A:
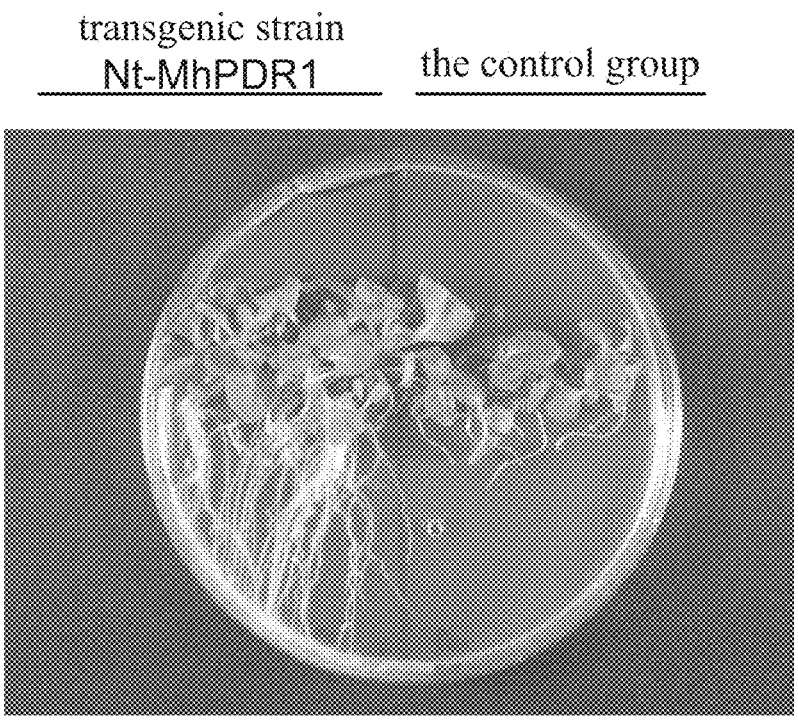
FIG. 5A: the root growing condition of Nt-MhPDR1-transferred seedling.
Figure 5B:
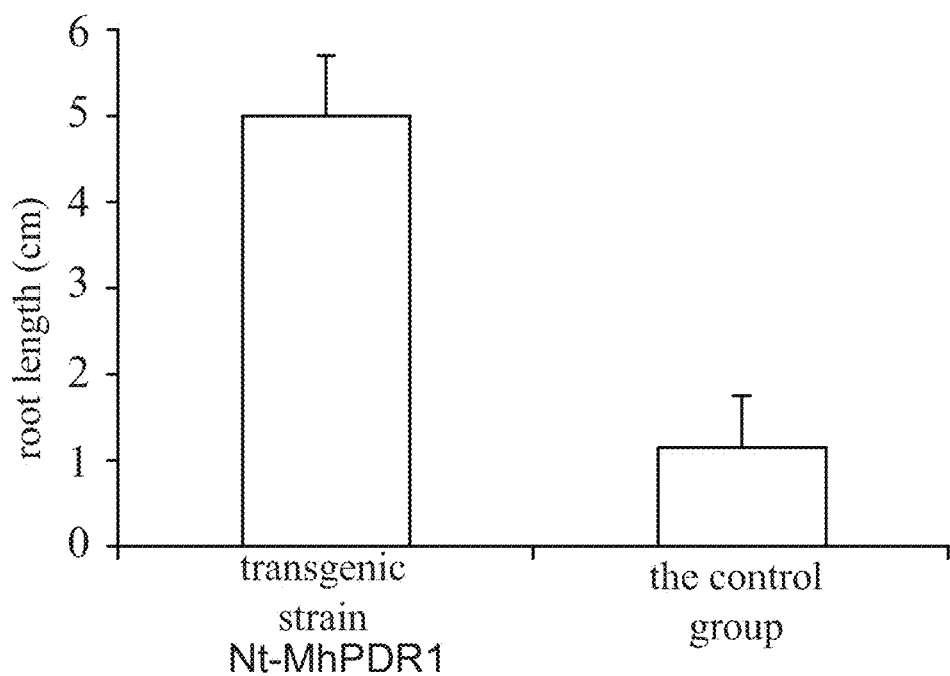
FIG. 5B: comparison of root lengths among Nt-MhPDR1-transferred seedlings.
Figure 5C:
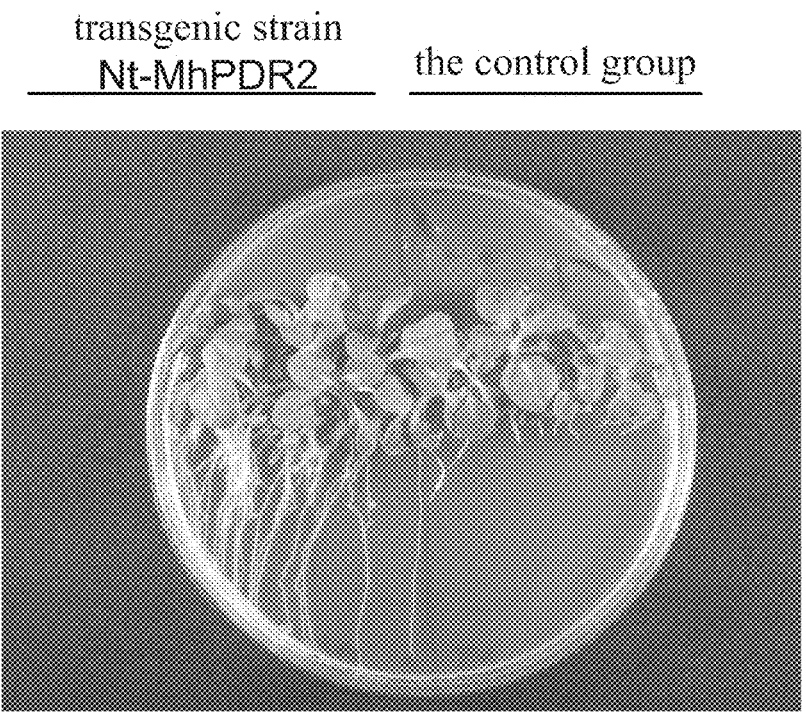
FIG. 5C: root growing conditions of Nt-MhPDR2-transferred seedlings.
Figure 5D:
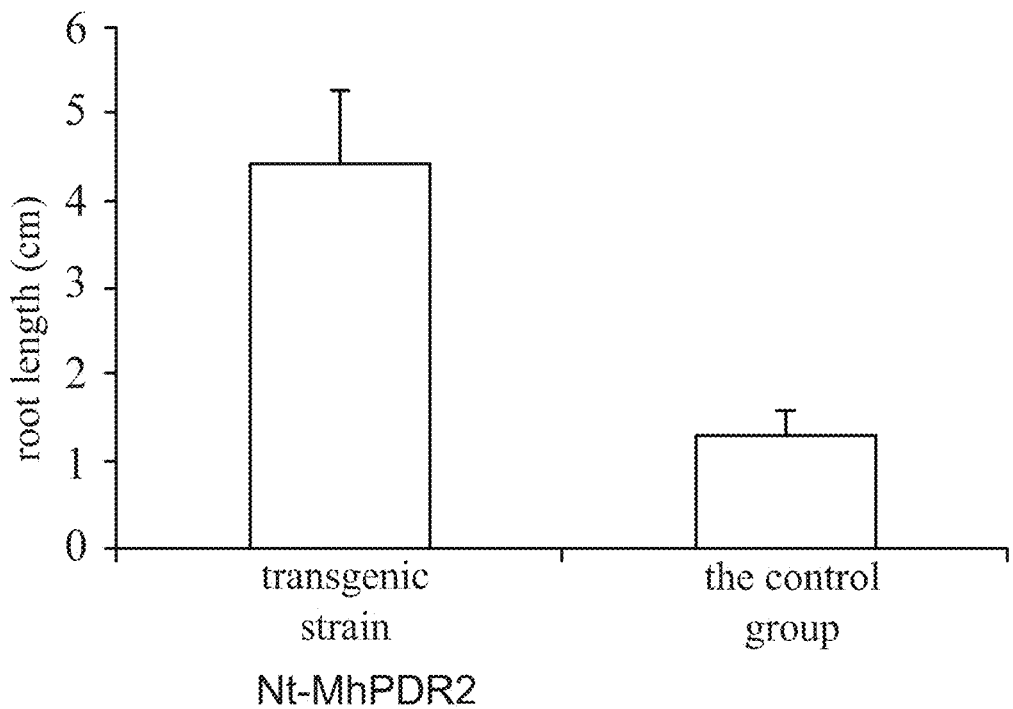
FIG. 5D: comparison on root lengths among Nt-MhPDR2-transferred seedlings.
Figure 6A:
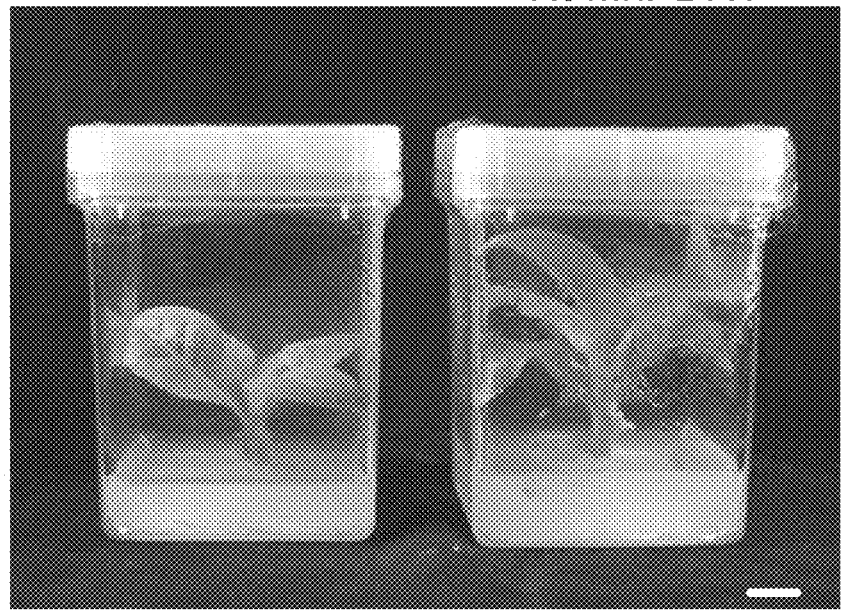
FIG. 6A: Nt-MhPDR1 one week after subculturing.
Figure 6B:
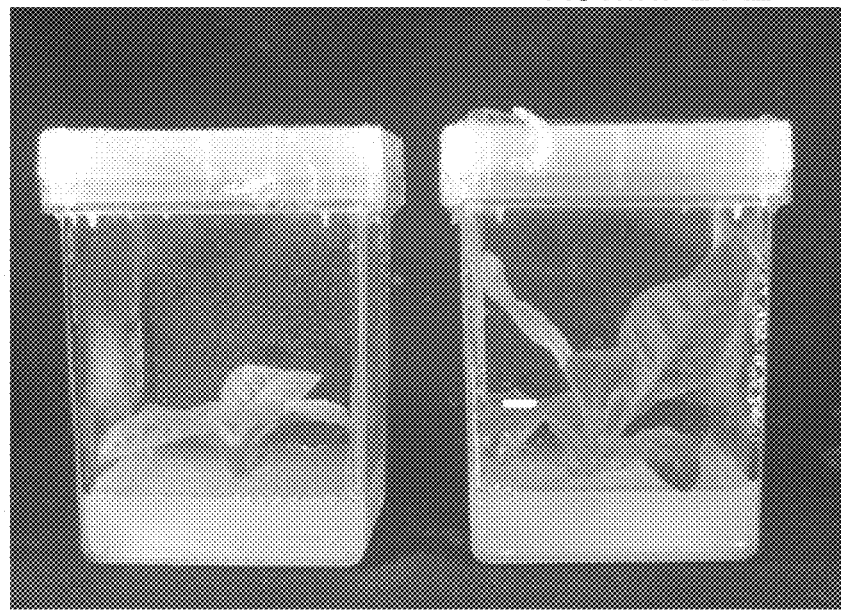
FIG. 6B: Nt-MhPDR2 one week after subculturing.
Figure 6C:
FIG. 6C: 3-month old Nt-MhPDR1.
Figure 6D:
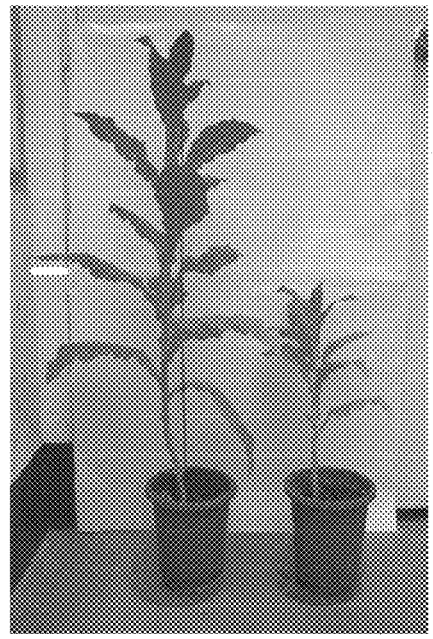
FIG. 6D: 3-month old Nt-MhPDR2.

Result of RT-PCR was shown in FIGS. 4A and 4B, wherein wild type tobacco (the control group) yielded no signal, while both transgenic strain Nt-MhPDR1 and Nt-MhPDR2 yielded predicted 0.46 kb hybridization signal. This indicated that both of these two genes could be over-expressed in transgenic strain under the activation of CaMV35S promoter, and could accumulate the product of the gene for promoting the rapid growth of a plant.

Example 5

The Transferred Gene could Promote Effectively the Nutritive Growth of the Transgenic Tobacco In order to observe external morphologies of transgenic strain Nt-MhPDR1 and Nt-MhPDR2, this Example performed two variation analysis: (1) root length of transgenic seedlings; and (2) height and leaf width increase of transgenic plant, and the results indicated that the transferred gene could promote effectively the nutritive growth of transgenic tobacco.

1. The Transferred Gene Could Promote Effectively the Root Growth of Transgenic Tobacco Seedlings Seeds of R2 generation tobacco transferred with gene for promoting rapid growth were cultivated in MS medium, and the medium was stood upright during the cultivation period. After four weeks, they were observed and their root lengths were measured. The results were shown in FIG. 5A to 5D. The observation of the growth condition of transgenic strain R2 generation seedlings revealed that, the average root length of the control group seedlings was 1.2 cm; average root length of Nt-MhPDR1 seedlings was 5.0 cm; and average root length of Nt-MhPDR2 seedlings was 4.4 cm. These remarkable differences demonstrated that the transferred gene could promote effectively the root growth of transgenic tobacco seedlings.

2. The Transferred Gene could Promote Effectively the Growth of Height and Leaf Width of Transgenic Tobacco Shoot apical meristem of transgenic strains Nt-MhPDR1 and Nt-MhPDR2 were cultivated in MS medium for 4 weeks, and then they were removed out of the bottle for growth variation analysis. The analytical method comprised of observing and recording their plant height and leaf width every week, wherein plant height was recorded as the measurement of the distance from ground surface to the growing point, while leaf width was measured as followed: the greatest width of the leaf was measured as X axis, then other width was measured as Y axis, the leaf width was calculated as [(X axis+Y axis)/2], the seedlings were removed out of the bottles after cottage for 4 weeks.

Figure 7A:
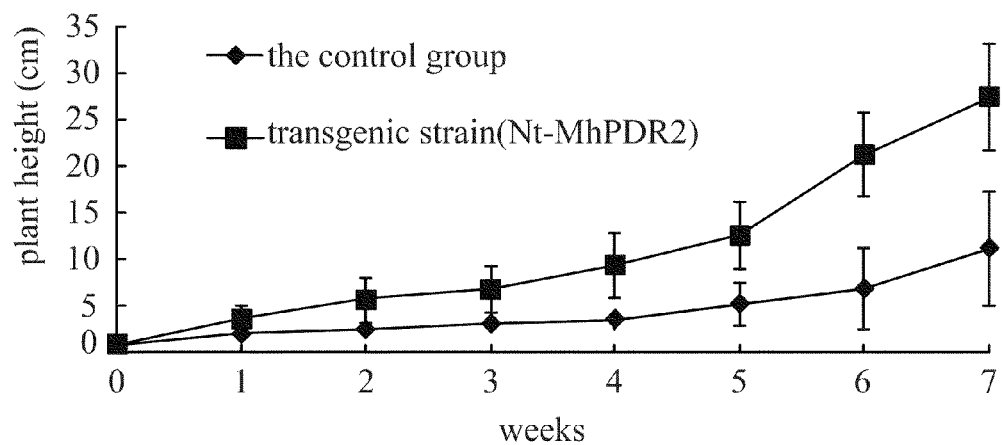
FIG. 7A: the height change of Nt-MhPDR2 transgenic strain.
Figure 7B:
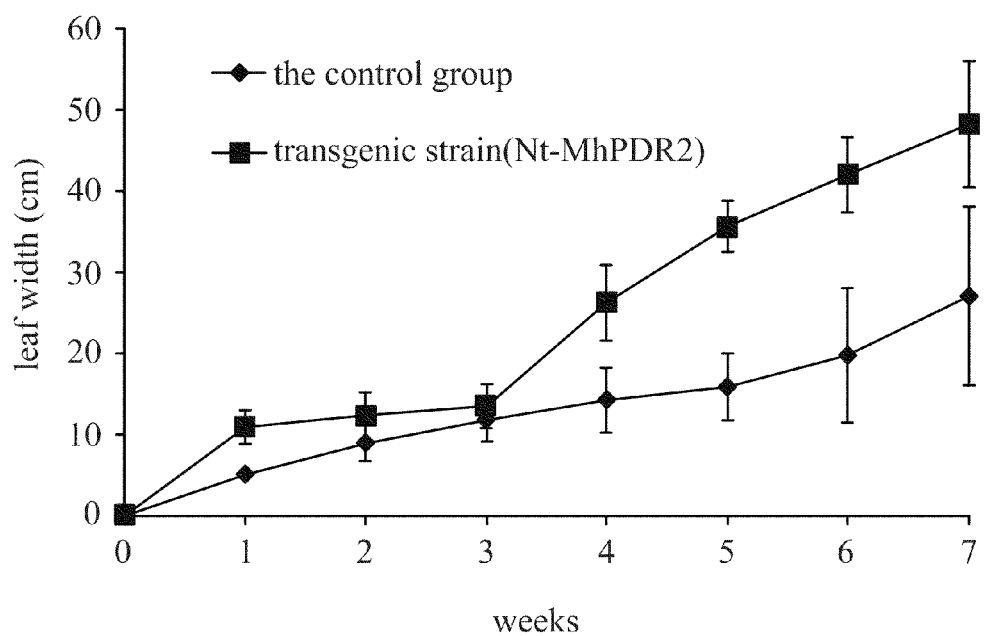
FIG. 7B: the leaf width change of Nt-MhPDR2 transgenic strain.

Results indicated that, compared with the control group, the growing potential of transgenic strain was better, as shown in FIG. 6A to 6D. Growing survey on Nt-MhPDR2 was further carried out, wherein plant height survey was shown in FIGS. 7A and 7B. On one week after removed out of the bottle, the average plant height of the control group was 2.2 cm; while the average plant height of MhPDR2 was 3.71 cm. The observation on the seventh week indicated that the average plant height of the control group was 11.3 cm; while the average plant height of MhPDR2 was 27.6 cm, and the average plant height difference was 16.3 cm. The survey result of leaf width was shown in FIG. 7B. On one week after removed out of the bottle, the average leaf width of the control group was 5.1 cm; the average leaf width of MhPDR2 was 11.0 cm. The observation on the seventh week indicated that, the average leaf width of the control group was 27.2 cm; while the average leaf width of MhPDR2 was 48.5 cm, and the leaf width difference was 21.3 cm. The plant height and leaf width had been subject to statistical analysis by Student's t-test, and all of the results indicated significant difference (*$P<0.05$). These demonstrated that the transferred gene could promote the nutritive growth of the transgenic tobacco.

Example 6

Figure 8A:
FIG. 8A: the blooming condition of 8-month old Nt-MhPDR1 transgenic strain; the control group (non-transferred strain) did not bloom yet.
Figure 8B:
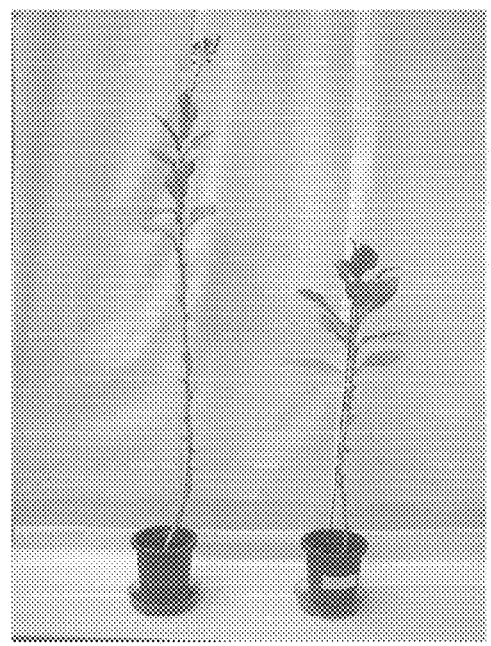
FIG. 8B: the blooming condition of 8-month old Nt-MhPDR2 transgenic strain, the control group (non-transferred strain) did not bloom yet.
Figure 10:
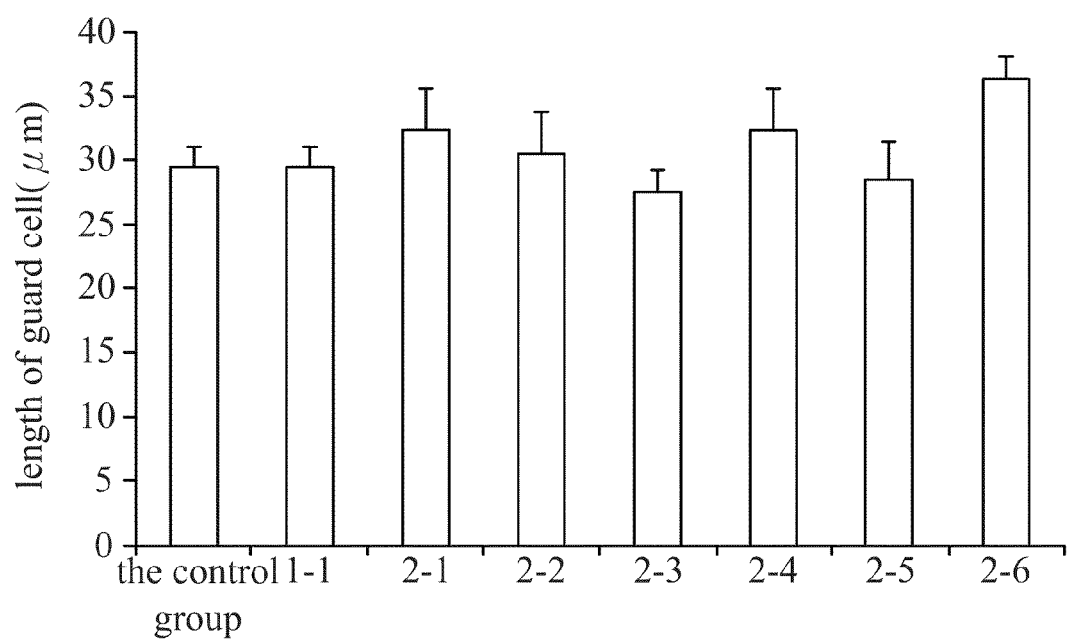
FIG. 10 shows the comparison of lengths of guard cells among over-expressed tobacco transgenic strains with vectors containing gene for promoting the rapid growth of a plant, no significant difference had been observed; wherein 1-1 represents Nt-MhPDR1-1 transgenic strain, 2-1 represents Nt-MhPDR2-1 transgenic strain; 2-2 represents Nt-MhPDR2-2 transgenic strain; 2-3 represents Nt-MhPDR2-3 transgenic strain; 2-4 represents Nt-MhPDR2-4 transgenic strain; 2-5 represents Nt-MhPDR2-5 transgenic strain; and 2-6 represents Nt-MhPDR2-6 transgenic strain.

Transferring Gene for Promote Rapid Growth could Advance the Blooming of the Transgenic Tobacco In order to observe the reproductive growth conditions of transgenic strain Nt-MhPDR1 and Nt-MhPDR2, this Example illustrated with figures that the transferred gene for promote rapid growth could promote, not only the nutritive growth rate such as root growth rate during seedling period, and plant height and leaf width of tobacco, but also could shorten time needed for blooming to advance into reproductive growth period. Source of plant material of non-transgenic strain was same as those of transgenic strain clone that was subjected early to *Agrobacterium* transfer. Plant material of non-transgenic strain was subjected to callus tissue induction of round leaf pieces simultaneously with transgenic strain, but not subjected to antibiotic screening. New buds were removed onto same medium to differentiate into full plants, which were removed out of the sterile bottles simultaneously with transgenic strain to carry out domestication and planting. Results were shown in FIGS. 8A and 8B, which revealed that transgenic tobacco transferred with gene for promoting the rapid growth of a plant could advance blooming time remarkably. On the eighth month, the inflorescence of the transgenic strain began to wither, and its seeds were ripened, while non-transgenic strain did not bloom yet.

Example 7

The Mechanism of the Gene for Promoting Rapid Growth

In order to define clearly whether the rapid growth of a plant caused by the gene for promoting the rapid growth of a plant was induced by the enlarging of cell volume or not, the size of cell was further observed. Tobacco was cut into leaf pieces of 0.5 cm×0.5 cm. Phosphate buffer (each liter containing 39 mL 0.2 M monobasic sodium phosphate, 61 mL 0.2 M dibasic sodium phosphate, pH 7.0) was used to formulate 2.5% Glutaraldehyde as immobilizing solution. Leaf pieces were immobilized in the immobilizing solution for 4 hour. The immobilizing solution was removed and phosphate buffer was added. The replacement was repeated for 6 times. Leaf pieces were fixed in 2% $OsO_4$ at 4° C. for 3 hours. The supernatant was discarded, and 30%, 50%, 70%, 80%, 95%, 100% were added successively to dehydrate. The supernatant was discarded, 100% acetone was added to carry out post-treatment. Leaf pieces were removed and dried by critical point drying (CPD). An aluminum stage sample made through gold cladding was placed in a S-3000N scanning electro microscope, and performed the scanning observation under an acceleration voltage of 15 KV.

The observation result of scanning electro microscope was shown in FIG. 9A to 9H, and FIG. 10. The average length of the control group guard cell was 29.45 μm, the average length of transgenic strain MhPDR1-1 guard cell was 29.45 μm, and the average length of transgenic strain MhPDR2-1~6 guard cell was 32.3, 30.4, 27.5, 32.3, 28.5 and 26.25 μm, all of these data did not show significant difference. Therefore, the better plant height and leaf width of transgenic strain tobacco containing gene for promoting rapid growth did not come from the enlarging of cell volume, but due to the increase of the whole number of cells.

Accordingly, it could be postulated that MhPDR gene might participated in the control of mechanisms associated with the growth and development of a plant, and might affect the growth and development through the control of nutritional elements, and allowed the growth potential of the transgenic strain become better than that of non-transgenic strain.

Many changes and modifications in the above described embodiments of the invention can, of course, be carried out without departing from the scope thereof. Accordingly, to promote the progress in science and the useful arts, the invention is disclosed and is intended to be limited only by the scope of the appended claims.

What is claimed is:

1. An isolated polynucleotide for promoting the rapid growth of a plant comprising a nucleic acid sequence encoding an ATP-binding cassette transporter comprising the amino acid sequence of SEQ ID NO: 1 or SEQ ID NO:3.

2. The polynucleotide of claim 1, wherein said polynucleotide comprises SEQ ID NO: 2 or SEQ ID NO: 4.

3. A recombinant plasmid comprising a nucleic acid sequence operably linked to the 3' end of a promoter, wherein said nucleic acid sequence encodes an ATP-binding cassette transporter comprising the amino acid sequence of SEQ ID NO: 1 or SEQ ID NO:3.

4. A plant, or part thereof, organ, tissue or cell of said plant containing the recombinant plasmid as recited in claim 3 constructed by gene transfer.

5. A method for promoting the rapid growth of a plant, comprising the following steps:
   step 1: providing a cell or tissue of a target plant;
   step 2: transforming the recombinant plasmid as recited in claim 3 into the cell or tissue of the target plant provided in step 1 to obtain a transgenic cell of said plant or a transgenic tissue of said plant; and
   step 3: cultivating the transgenic cell or transgenic tissue of said plant obtained in step 2 to produce a transgenic plant or part thereof, organ, tissue or cell of said transgenic plant containing the recombinant plasmid as recited in claim 3.

6. The method as recited in claim 5, wherein said transforming method described in step 2 comprises one selected from the group consisting of *Agrobacterium* mediation, genetic recombinant virus infection, transposon vector transferring, gene gun transferring, electroporation, microinjection, pollen tube pathway, liposome mediation, ultrasonic mediation, silicon carbide fiber-mediated transformation, electrophoresis, laser microbeam, polyethylene glycol (PEG), calcium phosphate transferring, and DEAE-dextran mediated transformation.

* * * * *

SEQUENCE LISTING

```
<160> NUMBER OF SEQ ID NOS: 10

<210> SEQ ID NO 1
<211> LENGTH: 1452
<212> TYPE: PRT
<213> ORGANISM: banana
<220> FEATURE:
<223> OTHER INFORMATION: Musa spp cv Hsien Jin Chiao AAA group

<400> SEQUENCE: 1

Met Glu Pro Ser Glu Val His Arg Ile Ala Ser Leu Arg Arg Asn Ser
1               5                   10                  15

Ser Ile Trp Lys Arg Asp Asp Asn Ile Phe Ser Arg Ser Ser Arg Asp
            20                  25                  30
```

-continued

Glu Asp Asp Glu Glu Ala Leu Lys Trp Ala Ala Leu Glu Lys Leu Pro
         35                  40                  45

Thr Phe Asp Arg Val Arg Arg Gly Ile Leu Thr Leu Ala Glu Asp Gly
 50                  55                  60

Arg Gln Leu Gln Glu Val Asp Val Gln Arg Leu Gly Phe Gln Glu Arg
 65                  70                  75                  80

Lys Thr Leu Met Glu Arg Leu Val Arg Val Ala Glu Glu Asp Asn Glu
                 85                  90                  95

Arg Phe Leu Leu Lys Leu Lys Asp Arg Ile Asp Arg Val Gly Ile Asp
                100                 105                 110

Leu Pro Thr Ile Glu Val Arg Tyr Glu His Leu Ser Ile Glu Ala Glu
            115                 120                 125

Thr His Val Gly Asn Arg Gly Leu Pro Thr Val Phe Asn Ser Val Ala
        130                 135                 140

Asn Val Leu Glu Thr Ala Ala Asn Tyr Leu His Ile Leu Pro Ser Arg
145                 150                 155                 160

Lys Lys Pro Leu Ser Ile Leu His Asp Val Asn Gly Ile Ile Lys Pro
                165                 170                 175

Arg Arg Met Thr Leu Leu Leu Gly Pro Pro Gly Ser Gly Lys Thr Thr
                180                 185                 190

Leu Leu Leu Ala Leu Ala Gly Lys Leu Ser Ser Asp Leu Lys Thr Ser
            195                 200                 205

Gly Lys Val Thr Tyr Asn Gly His Glu Met Lys Glu Phe Val Pro Gln
210                 215                 220

Arg Thr Ala Ala Tyr Ile Ser Gln Tyr Asp Leu His Ile Gly Glu Met
225                 230                 235                 240

Thr Val Arg Glu Thr Leu Ala Phe Ser Ala Arg Cys Gln Gly Val Gly
                245                 250                 255

Thr Arg Tyr Asp Met Leu Thr Glu Leu Ala Arg Arg Glu Lys Ala Ala
            260                 265                 270

Asn Ile Lys Pro Asp Pro Asp Val Asp Val Phe Met Lys Ala Ser Ala
        275                 280                 285

Met Lys Gly Gln Glu Thr Asn Val Thr Thr Asp Tyr Ile Leu Lys Ile
290                 295                 300

Leu Gly Leu Glu Val Cys Ala Asp Thr Met Val Gly Asp Glu Met Leu
305                 310                 315                 320

Arg Gly Ile Ser Gly Gly Gln Arg Lys Arg Val Thr Thr Gly Glu Met
                325                 330                 335

Leu Val Gly Pro Ala Arg Ala Leu Phe Met Asp Glu Ile Ser Thr Gly
            340                 345                 350

Leu Asp Ser Ser Thr Thr Phe Gln Ile Val Asn Ser Leu Arg Gln Thr
        355                 360                 365

Ile His Ile Leu Gly Gly Thr Ala Val Ile Ser Leu Leu Gln Pro Ala
    370                 375                 380

Pro Glu Thr Tyr Asp Leu Phe Asp Ile Ile Leu Leu Ser Asp Gly
385                 390                 395                 400

Leu Ile Val Tyr Gln Gly Pro Arg Glu Asn Val Val Glu Phe Phe Glu
                405                 410                 415

Ser Met Gly Phe Lys Cys Pro Glu Arg Met Gly Val Ala Asp Phe Leu
            420                 425                 430

Gln Glu Val Thr Ser Arg Lys Asp Gln Gln Tyr Trp Ser Arg Gln
        435                 440                 445

Asp Glu Pro Tyr Arg Tyr Val Pro Val Arg Glu Phe Ala Glu Ala Phe

-continued

```
                450                 455                 460
Gln Gln Phe His Ile Gly Arg Ala Leu Ala Glu Glu Leu Ser Val Pro
465                 470                 475                 480

Phe Asp Lys Ser Lys Ser His Pro Ala Ala Leu Thr Thr Thr Arg Tyr
                485                 490                 495

Gly Val Ser Lys Lys Glu Val Leu Lys Ala Asn Met Ala Arg Glu Leu
                500                 505                 510

Leu Leu Met Lys Arg Asn Ser Phe Val Tyr Ile Phe Lys Ala Val Gln
                515                 520                 525

Leu Val Ile Met Ala Val Ile Ala Met Thr Val Phe Leu Arg Thr Lys
530                 535                 540

Met His Arg Asn Asp Ile Asp Asp Gly Met Ile Tyr Asn Gly Ala Leu
545                 550                 555                 560

Phe Tyr Gly Ile Val Thr Ile Met Phe Asn Gly Phe Ser Glu Leu Ala
                565                 570                 575

Met Thr Ile Met Lys Leu Pro Val Phe Phe Lys Gln Arg Asp Leu Leu
                580                 585                 590

Phe Tyr Pro Ala Trp Ser Tyr Thr Ile Pro Ala Trp Ile Leu Lys Ile
                595                 600                 605

Pro Ile Ala Phe Ala Glu Val Ala Val Trp Val Phe Thr Thr Tyr Tyr
610                 615                 620

Val Ile Gly Phe Asp Pro Asn Val Gly Arg Leu Phe Lys Gln Tyr Leu
625                 630                 635                 640

Leu Leu Leu Val Thr Asn Gln Met Ala Ser Gly Leu Phe Arg Thr Ile
                645                 650                 655

Gly Ala Val Gly Arg Asn Met Ile Val Ala Asn Thr Phe Gly Ala Phe
                660                 665                 670

Ala Leu Leu Ile Leu Leu Val Leu Gly Gly Phe Ile Leu Ser Arg Glu
                675                 680                 685

Lys Val Lys Lys Trp Trp Ile Trp Gly Tyr Trp Ile Ser Pro Leu Met
                690                 695                 700

Tyr Pro Gln Asn Ala Ile Ser Val Asn Glu Phe Leu Gly His Ser Trp
705                 710                 715                 720

Ser His Ile Pro Ser Asn Leu Asn Ser Thr Glu Pro Leu Gly Val Thr
                725                 730                 735

Val Leu Glu Ser Arg Gly Ile Phe Ala Glu Ala Lys Trp Tyr Trp Ile
                740                 745                 750

Gly Leu Gly Ala Thr Val Gly Tyr Val Leu Leu Phe Asn Ala Leu Phe
                755                 760                 765

Thr Leu Ala Leu Thr Tyr Leu Asp Pro Phe Gly Lys Ser Gln Pro Pro
770                 775                 780

Leu Ser Glu Glu Thr Leu Lys Glu Lys His Ala Asn Leu Thr Gly Glu
785                 790                 795                 800

Val Leu Glu Asn Ser Ser Arg Gly Arg Arg Ser Val Arg His Ser Ala
                805                 810                 815

Ser Lys Lys Ser Ala Ser Gly Ile Gly Arg Lys Ser Ser Leu Gly
                820                 825                 830

Ser Met Arg Ala Ala Phe Glu Gln Asn Lys Lys Gly Met Val Leu Pro
835                 840                 845

Phe Thr Pro Leu Ser Ile Thr Phe Asp Asp Val Arg Tyr Ser Val Asp
                850                 855                 860

Met Pro Gln Glu Met Lys Ala Gln Gly Val Val Glu Asp Arg Leu Glu
865                 870                 875                 880
```

```
Leu Leu Lys Gly Val Ser Gly Ser Phe Arg Pro Val Leu Thr Ala
                885                 890                 895

Leu Met Gly Val Ser Gly Ala Gly Lys Thr Thr Leu Met Asp Val Leu
            900                 905                 910

Ala Gly Arg Lys Thr Gly Gly Tyr Ile Glu Gly Asp Ile Ser Ile Ser
            915                 920                 925

Gly Tyr Pro Lys Lys Gln Glu Thr Phe Ala Arg Ile Ser Gly Tyr Cys
            930                 935                 940

Glu Gln Asn Asp Ile His Ser Pro His Val Thr Val Gln Glu Ser Leu
945                 950                 955                 960

Ala Tyr Ser Ala Trp Leu Arg Leu Pro Ser Glu Val Asp Ser Glu Thr
                965                 970                 975

Arg Lys Met Phe Val Glu Glu Val Met Glu Leu Val Glu Leu Thr Pro
            980                 985                 990

Leu Arg Asp Ala Leu Val Gly Leu Pro Gly Val Asp Gly Leu Ser Thr
            995                 1000                1005

Glu Gln Arg Lys Arg Leu Thr Ile Ala Val Glu Leu Val Ala Asn Pro
            1010                1015                1020

Ser Ile Ile Phe Met Asp Glu Pro Thr Ser Gly Leu Asp Ala Arg Ala
1025                1030                1035                1040

Ala Ala Ile Val Met Arg Ala Val Arg Asn Thr Val Asp Thr Gly Arg
            1045                1050                1055

Thr Val Val Cys Thr Ile His Gln Pro Ser Ile Asp Ile Phe Glu Ala
            1060                1065                1070

Phe Asp Glu Leu Phe Leu Leu Lys Arg Gly Gly Glu Glu Ile Tyr Val
            1075                1080                1085

Gly Pro Leu Gly Arg Asp Ser Ser His Leu Ile Ser Tyr Phe Glu Gly
            1090                1095                1100

Ile Asn Gly Ile Ser Lys Ile Lys Asp Gly Tyr Asn Pro Ala Thr Trp
1105                1110                1115                1120

Met Leu Glu Val Thr Ser Gln Ala Gln Glu Asn Ile Leu Gly Ala Asn
            1125                1130                1135

Phe Asn Glu Ile Tyr Arg Asn Ser Glu Leu Tyr Arg Arg Asn Lys Ser
            1140                1145                1150

Leu Ile Lys Asp Leu Ser Ile Pro Pro Ala Gly Ser Ser Asp Leu Tyr
            1155                1160                1165

Phe Pro Thr Gln Tyr Ser Gln Ser Phe Pro Val Gln Cys Met Ala Cys
            1170                1175                1180

Leu Trp Lys Gln His Leu Ser Tyr Trp Arg Asn Pro Pro Tyr Thr Ala
1185                1190                1195                1200

Val Arg Phe Phe Phe Thr Thr Ile Val Ala Leu Leu Phe Gly Thr Ile
            1205                1210                1215

Phe Trp Asp Leu Gly Gly Lys Met Asn Thr Gln Gln Asp Leu Phe Asn
            1220                1225                1230

Ala Met Gly Ser Met Tyr Ala Ala Val Leu Phe Met Gly Ile Gln Asn
            1235                1240                1245

Cys Ser Ser Val Gln Pro Val Val Ala Val Glu Arg Thr Val Phe Tyr
            1250                1255                1260

Arg Glu Lys Ala Ala Gly Met Tyr Ser Ala Leu Pro Tyr Ala Phe Gly
1265                1270                1275                1280

Gln Val Ala Ile Glu Leu Pro Tyr Ile Leu Cys Gln Ser Ala Leu Tyr
            1285                1290                1295

Gly Val Ile Val Tyr Ala Met Ile Gly Phe Glu Trp Thr Val Ala Lys
            1300                1305                1310
```

```
Phe Phe Trp Tyr Leu Phe Phe Met Tyr Phe Thr Leu Leu Tyr Phe Thr
        1315                1320                1325
Phe Tyr Gly Met Met Ala Val Gly Ile Thr Pro Asn His Ser Ile Ala
    1330                1335                1340
Ser Ile Val Ser Ala Phe Tyr Ala Ile Trp Asn Leu Phe Ser Gly
1345                1350                1355                1360
Phe Ile Ile Pro Arg Pro Arg Ile Pro Val Trp Trp Arg Trp Tyr Tyr
            1365                1370                1375
Trp Ala Cys Pro Val Ala Trp Thr Leu Tyr Gly Leu Val Ala Ser Gln
        1380                1385                1390
Phe Gly Asp Ile Glu Thr Ile Met Asp Asp Lys Asn Val Pro Val Ser
        1395                1400                1405
Glu Phe Leu Arg Ser Tyr Phe Gly Phe Lys His Ser Phe Leu Gly Val
            1410                1415                1420
Val Ala Ala Val Val Ala Phe Pro Val Met Phe Ala Phe Leu Phe
1425                1430                1435                1440
Ala Phe Ser Ile Lys Met Leu Asn Phe Gln Lys Arg
            1445                1450

<210> SEQ ID NO 2
<211> LENGTH: 4731
<212> TYPE: DNA
<213> ORGANISM: banana
<220> FEATURE:
<223> OTHER INFORMATION: Musa spp cv Hsien Jin Chiao AAA group

<400> SEQUENCE: 2
tgtctgtctc tctctctctc catcgcaagc aaagaaggga gacaaaatta agaggcggag      60
gaagaggagc ggaagaacag cggcttcggt tttggctctc gttctttct tgtgatcatc      120
attcataagg attttgcgtt ggttggaaaa ggaggcgcag gccggcggag agaggggag      180
agaggtggag atggaaccga gcgaggtgca caggatcgcg agcttgcgaa ggaatagttc      240
gatatggaag agggacgata acatcttctc gcggtcgtcg cgggacgaag acgacgagga      300
ggccctcaag tgggccgccc tcgagaagct gcccaccttc gaccgcgtgc gccgtggcat      360
cctgacgctg gccgaggatg gcaggcagct gcaagaggtc gacgtccagc ggctcggctt      420
ccaggagagg aagaccctca tggagcgcct cgttcgggtc gccgaggagg acaatgagcg      480
tttcttgctc aagctcaagg accgtatcga ccgagttggg attgatcttc ccaccatcga      540
agtgcggtat gagcacctaa gcatcgaagc agagacacac gtgggcaaca gaggattgcc      600
taccgtcttc aattccgtcg ctaacgtact ggagaccgcc gcaaattact gcacatact      660
accgagtaga aagaaacctt tatcgatcct tcatgacgtc aatggaatca tcaaacctcg      720
caggatgact tgctcttag gtcctccagg atcaggaaaa actacactgt tgttggcttt      780
ggctggaaag ctcagctctg atttgaagac ctccggaaaa gtgacctaca acggtcatga      840
aatgaaagaa ttcgtccctc agagaaccgc tgcatacatc agccagtatg atcttcatat      900
aggggagatg acagtccgtg aaacattagc ccttctgcg aggtgccaag agttggcac      960
tcgttatgat atgttaactg agttagctag gagagagaag gcagcaaaca tcaagccaga     1020
tccagacgta gatgtcttca tgaaggcatc tgcaatgaaa ggacaagaaa ccaatgtgac     1080
cacagactac atactgaaga tcctgggttt ggaggtctgt gctgacacga tggtaggaga     1140
tgagatgctg agaggcatct ctggtggaca aggaagcgt gtcaccacag gtgaaatgct     1200
tgttggacct gcaagagctc tgttcatgga tgagatatcg actggtctgg atagctcaac     1260
```

```
gactttccag atagtgaact cgctcaggca aaccatccac attcttggag ggactgctgt   1320
tatctccctg ctgcagccag caccggagac gtatgacctt ttcgacgaca tcattcttct   1380
ctccgatggc ctgatcgtgt atcaaggccc tcgtgaaaat gtcgtcgagt tcttcgagtc   1440
catgggcttc aagtgcccag agaggatggg tgttgcggac ttcctgcaag aagtaacgtc   1500
gaggaaggat caacaacagt actggtcacg ccaggatgaa ccttacagat acgtgcccgt   1560
tagagaattt gccgaggcat tccaacaatt ccatattggt cgggctttag ccgaagaact   1620
ttctgtcccg tttgataaga gcaagagcca tcctgctgct cttaccacca cgagatatgg   1680
ggtgagcaag aaggaggtgt taaaagcaaa catggccaga gaactattgc tgatgaagag   1740
gaactcgttc gtctacatct tcaaggccgt tcaacttgtc atcatggcgg tcattgcgat   1800
gacggtgttt ctgcgtacta agatgcaccg gaacgatata gatgacggga tgatctataa   1860
tggcgcgctt ttctatggga tagtgacgat catgttcaac gggttctctg aacttgccat   1920
gaccattatg aagctacctg ttttcttcaa gcagagagat ctccttttct atcccgcatg   1980
gtcatacaca ataccccgcat ggatccttaa gatccccatt gcatttgctg aagttgcagt   2040
gtgggttttc acaacctact acgtcattgg attcgatcca aatgttggaa ggctgttcaa   2100
gcaatacctg ctgctgctgg tgacgaacca gatggcatct ggactcttcc gcaccatcgg   2160
ggccgtcggg aggaacatga tagtggcaaa taccttcggg gcttttgctc ttctcattct   2220
tctggtgctg ggtggcttca ttctttcacg agagaaagtg aagaaatggt ggatttgggg   2280
ctactggatc tcgccgctga tgtacccca gaacgcaatc tcagtgaatg aattcttggg   2340
gcacagctgg agtcatattc cttcgaattt gaattcaaca gagccgctgg gagtcacagt   2400
tctggagtcc cgtggtatct ttgccgaagc caaatggtat tggattggcc ttggggctac   2460
ggtcggctac gtacttctct tcaatgctct tttcactttg gctctcactt acctcgatcc   2520
ttttgggaaa tctcagccac ctctatctga agagaccta aaggagaaac acgccaatct   2580
aaccggagaa gtgttggaga actcgtccag aggaagaaga tccgtgcgtc actctgcatc   2640
caagaagagc gcgagtggga tagggaggaa gagcagctca ttgggttcca tgagggcggc   2700
cttcgaacag aacaagaagg gaatggtcct tccgtttact ccactgtcca tcaccttcga   2760
cgacgtgagg tactctgtgg acatgccgca ggaaatgaaa gctcaaggtg tggttgaaga   2820
ccggttggag ctgctgaagg gcgtcagtgg atcttcagg ccgggagtgc ttacagctct   2880
aatgggggtg agtggagctg gcaaaacgac gctgatggat gtgctggctg ggagaaagac   2940
aggggggatac attgaaggag acatcagcat atctggctac cccaagaagc aggagacctt   3000
tgctcgcatc tcgggatact gcgaacagaa cgacatccac tctcctcatg tcacggttca   3060
ggagtctctc gcctactcgg cgtggctccg gttaccttct gaggtcgatt ctgaaacgag   3120
gaagatgttc gtggaggagg tcatggagct ggtagagctg acgccgctga gggatgcact   3180
cgtcgggttg ccgggagtag atgggttatc gacagagcaa cggaagaggt tgaccatcgc   3240
tgtggagctg gtcgccaacc catcgatcat attcatggat gaacccacct ctgggcttga   3300
cgcaagggcc gccgccattg tcatgagagc cgtgaggaac acagtggaca ccggaaggac   3360
tgtggtgtgt accattcacc aacccagcat cgacatattt gaagctttcg atgagctctt   3420
cttattaaag cgtggcgggg aagagatata tgtgggtccg ctcggtcgtg actcttccca   3480
tctgattagc tattttgagg gaatcaatgg tatcagtaag atcaaagatg gttacaaccc   3540
cgcgacatgg atgttggaag tgacttcgca ggcacaagaa aatatactgg gcgccaatt   3600
caatgagata tacaggaatt cggagctgta tcggaggaac aagagcttga taaaggatct   3660
```

```
cagcatacct cctgctggtt cgagcgacct gtacttcccc acccagtact cgcagtcatt   3720
tcctgtacaa tgcatggcgt gcctgtggaa gcagcacttg tcgtactgga ggaatccgcc   3780
gtacaccgcc gtgaggttct tcttcaccac catcgtagct cttctgttcg gcaccatatt   3840
ctgggacctg gcggcaaaa tgaacactca gcaagatctg tttaatgcga tgggttcgat   3900
gtatgccgcg gttctgttca tgggtataca gaactgttca tcggttcagc cggtggtggc   3960
agtcgaacga acagtctttt acagggagaa agcggctgga atgtactccg ctttgcctta   4020
cgcgttcgga caagtggcga ttgagcttcc atacattctg tgtcagtccg ccctatatgg   4080
tgtgatcgtc tacgcgatga ttggattcga gtggactgtt gcaaagttct tttggtactt   4140
gttcttcatg tacttcactc tcctctactt cacattctac gggatgatgg cggtgggtat   4200
cactcccaat cacagcatcg cctccattgt ttccgctttc ttctacgcaa tatggaacct   4260
tttctctgga ttcattattc cgcggccgag aatcccggtg tggtggagat ggtattactg   4320
ggcgtgtccc gtagcttgga ccttgtacgg tctagtcgcc tcacagttcg gtgatataga   4380
gactatcatg gatgacaaga acgtgccggt gtcagagttc ttgaggagtt attttggatt   4440
caaacatagc ttcttggggg tggtggctgc cgtggtggtg gcgtttcctg tgatgtttgc   4500
tttcctcttt gcattttcca tcaagatgct caacttccag aagagatgaa gatgggattg   4560
cctgcctgcc tgccaaggat ctacaaagat atgagagatg tccttgcaac cgaaccatat   4620
acatatatat gcctatataa ttgacatttg taattttggg atatttatta ttgtattatg   4680
aatgaattga ttgccatcaa tgaacaacgg aaatcaccaa tataaccgag a             4731
```

<210> SEQ ID NO 3
<211> LENGTH: 1468
<212> TYPE: PRT
<213> ORGANISM: banana
<220> FEATURE:
<223> OTHER INFORMATION: Musa spp cv Hsien Jin Chiao AAA group

<400> SEQUENCE: 3

```
Met Glu Pro Ser Glu Val Leu Arg Ile Gly Ser Leu Arg Arg Asn Ser
1               5                   10                  15

Ser Val Trp Arg Arg Gly Asp Glu Ser Ile Phe Ser Arg Ser Ser Arg
            20                  25                  30

Asp Glu Asp Asp Glu Glu Ala Leu Lys Trp Ala Ala Leu Glu Lys Leu
        35                  40                  45

Pro Thr Phe Asp Arg Val Arg Arg Gly Ile Leu Ala Leu Ala Glu Asp
    50                  55                  60

Gly Gly Glu Leu Gln Glu Val Asn Ile Glu Arg Leu Gly Phe Arg Glu
65                  70                  75                  80

Lys Lys Ala Leu Ile Glu Arg Leu Val Arg Val Ala Asp Glu Asp Asn
                85                  90                  95

Glu Arg Phe Leu Leu Lys Leu Arg Asp Arg Val Asp Arg Val Gly Ile
            100                 105                 110

Asp Leu Pro Thr Ile Glu Val Arg Tyr Glu His Leu Ser Ile Glu Ala
        115                 120                 125

Glu Thr Tyr Val Gly Asn Arg Gly Leu Pro Thr Ile Phe Asn Ser Thr
    130                 135                 140

Leu Asn Met Leu Glu Ala Phe Gly Asn Tyr Leu Arg Val Leu Pro Ser
145                 150                 155                 160

Arg Lys Arg Pro Leu Ser Ile Leu His Asp Val Ser Gly Ile Ile Lys
                165                 170                 175

Pro Arg Thr Met Ala Leu Leu Leu Gly Pro Pro Gly Ser Gly Lys Thr
```

```
                    180                 185                 190
Thr Leu Leu Leu Ala Leu Ala Gly Lys Leu Ser Ser Asp Leu Lys Val
                195                 200                 205

Thr Gly Lys Val Thr Tyr Asn Gly His Asp Met Ser Glu Phe Val Pro
                210                 215                 220

Gln Arg Thr Ala Ala Tyr Ile Ser Gln Tyr Asp Leu His Ile Gly Glu
225                 230                 235                 240

Met Thr Val Arg Glu Thr Leu Ala Phe Ser Ala Arg Cys Gln Gly Val
                245                 250                 255

Gly Thr Arg Tyr Glu Met Leu Thr Glu Leu Ala Arg Arg Glu Lys Ala
                260                 265                 270

Ala Asn Ile Lys Pro Asp Pro Asp Ile Asp Val Phe Met Lys Ala Ser
                275                 280                 285

Ser Met Lys Gly Gln Glu Ala Asn Val Ile Thr Glu Tyr Ile Leu Lys
                290                 295                 300

Ile Leu Gly Leu Glu Val Cys Ala Asp Thr Met Val Gly Asp Glu Met
305                 310                 315                 320

Leu Arg Gly Ile Ser Gly Gly Gln Arg Lys Arg Val Thr Thr Gly Glu
                325                 330                 335

Met Leu Val Gly Pro Ala Arg Ala Leu Phe Met Asp Glu Ile Ser Thr
                340                 345                 350

Gly Leu Asp Ser Ser Thr Thr Phe Gln Ile Val Asn Ser Leu Arg Gln
                355                 360                 365

Thr Ile His Ile Leu Ser Gly Thr Ala Met Ile Ser Leu Leu Gln Pro
                370                 375                 380

Ala Pro Glu Thr Tyr Asp Leu Phe Asp Asp Ile Ile Leu Leu Ser Asp
385                 390                 395                 400

Gly Leu Ile Val Tyr Gln Gly Pro Arg Asp Asn Val Leu Glu Phe Phe
                405                 410                 415

Glu Ser Met Gly Phe Arg Cys Pro Glu Arg Lys Gly Val Ala Asp Phe
                420                 425                 430

Leu Gln Glu Val Thr Ser Arg Lys Asp Gln Gln Gln Tyr Trp Ala Arg
                435                 440                 445

Gln Asp Glu Pro Tyr Arg Tyr Val Pro Val Arg Glu Phe Ala Glu Ala
                450                 455                 460

Phe Gln Ser Phe His Val Gly Arg Ala Leu Gly Asp Glu Leu Ser Val
465                 470                 475                 480

Pro Phe Asp Lys Thr Lys Ser His Pro Ala Ala Leu Thr Thr Thr Arg
                485                 490                 495

Tyr Gly Val Ser Lys Lys Glu Val Leu Lys Ala Asn Ile Asp Arg Glu
                500                 505                 510

Leu Leu Leu Met Lys Arg Asn Ser Phe Val Tyr Ile Phe Lys Ala Thr
                515                 520                 525

Gln Leu Thr Ile Met Ala Ile Val Ser Met Thr Val Phe Leu Arg Thr
                530                 535                 540

Lys Met Pro Arg Glu Thr Glu Thr Asp Gly Leu Thr Tyr Leu Gly Ala
545                 550                 555                 560

Leu Phe Phe Ser Val Val Met Val Met Phe Asn Gly Phe Ser Glu Leu
                565                 570                 575

Ala Met Thr Ile Met Lys Leu Pro Val Phe Phe Lys Gln Arg Asp Leu
                580                 585                 590

Leu Phe Tyr Pro Ala Trp Ser Tyr Thr Ile Pro Thr Trp Ile Leu Lys
                595                 600                 605
```

```
Ile Pro Ile Ala Phe Val Glu Val Ala Val Trp Val Phe Thr Thr Tyr
610                 615                 620

Tyr Val Ile Gly Phe Asp Pro Asn Val Gly Arg Leu Phe Lys Gln Tyr
625                 630                 635                 640

Leu Leu Leu Leu Gly Ile Thr Gln Met Ala Ser Ala Val Phe Arg Thr
                645                 650                 655

Ile Gly Ala Leu Gly Arg Asn Met Ile Val Ala Asn Thr Phe Ala Ser
            660                 665                 670

Leu Ser Leu Leu Ile Leu Leu Val Leu Gly Gly Phe Ile Leu Ser Arg
        675                 680                 685

Glu Gln Val Lys Lys Trp Trp Ile Trp Gly Tyr Trp Ile Ser Pro Leu
690                 695                 700

Thr Tyr Ala Gln Asn Ala Ile Ser Val Asn Glu Phe Met Gly Asn Asn
705                 710                 715                 720

Trp Lys His Thr Ala Pro Gly Ser Asn Glu Ser Leu Gly Val Arg Val
                725                 730                 735

Leu Lys Ser Arg Gly Val Phe Pro Glu Ala Arg Trp Tyr Trp Ile Gly
            740                 745                 750

Phe Gly Ala Leu Val Gly Tyr Val Leu Leu Phe Asn Ala Leu Phe Thr
        755                 760                 765

Leu Ala Leu Ser Tyr Leu Asp Pro Phe Gly Lys Ser Gln Pro Pro Ile
770                 775                 780

Ser Glu Glu Thr Leu Lys Glu Lys His Ile Asn Leu Thr Gly Glu Gly
785                 790                 795                 800

Leu Glu Ser Ser Ser Arg Gly Arg Lys Ser Ile Asp His Ser Ala Ser
                805                 810                 815

Lys Ser Lys Ser Arg Gly His Ala Lys Ser Met Leu Ser Lys Ser Arg
            820                 825                 830

Arg Ala Gly Ser Glu Asn Gly Met Arg Arg Lys Asp Ser Ser Leu Gly
        835                 840                 845

Ser Met Lys Ala Ala Phe Asp Gln Asn Arg Arg Gly Met Val Leu Pro
850                 855                 860

Phe Thr Pro Leu Ser Ile Thr Phe Asp Asp Ile Arg Tyr Ser Val Asp
865                 870                 875                 880

Met Pro Gln Glu Met Lys Ala Gln Gly Val Ala Glu Asp Arg Leu Glu
                885                 890                 895

Leu Leu Lys Gly Val Ser Gly Ser Phe Arg Pro Gly Val Leu Thr Ala
            900                 905                 910

Leu Met Gly Val Ser Gly Ala Gly Lys Thr Thr Leu Met Asp Val Leu
        915                 920                 925

Ala Gly Arg Lys Thr Gly Gly Tyr Ile Glu Gly Asn Ile Asn Ile Ser
930                 935                 940

Gly Tyr Pro Lys Lys Gln Glu Thr Phe Ala Arg Ile Ser Gly Tyr Cys
945                 950                 955                 960

Glu Gln Asn Asp Ile His Ser Pro His Val Thr Val Tyr Glu Ser Ile
                965                 970                 975

Val Tyr Ser Ala Trp Leu Arg Leu Pro Pro Glu Val Asp Ser Glu Thr
            980                 985                 990

Arg Lys Met Phe Val Asp Glu Val Met Glu Leu Val Glu Leu Thr Pro
        995                 1000                1005

Leu Arg Asp Ala Leu Val Gly Leu Pro Gly Val Asp Gly Leu Ser Thr
1010                1015                1020

Glu Gln Arg Lys Arg Leu Thr Ile Ala Val Glu Leu Val Ala Asn Pro
1025                1030                1035                1040
```

```
Ser Ile Ile Phe Met Asp Glu Pro Thr Ser Gly Leu Asp Ala Arg Ala
            1045                1050                1055

Ala Ala Ile Val Met Arg Thr Val Arg Asn Thr Val Asp Thr Gly Arg
        1060                1065                1070

Thr Val Val Cys Thr Ile His Gln Pro Ser Ile Asp Ile Phe Glu Ala
        1075                1080                1085

Phe Asp Glu Leu Phe Leu Leu Lys Arg Gly Glu Glu Ile Tyr Ala
    1090                1095                1100

Gly Pro Leu Gly Arg His Ser Cys His Leu Ile Asp Tyr Phe Glu Gly
1105                1110                1115                1120

Ile Asn Gly Val Ser Lys Ile Lys Asp Gly Tyr Asn Pro Ala Thr Trp
                1125                1130                1135

Met Leu Glu Val Thr Thr Gln Ala Gln Glu Gly Ile Leu Gly Val Asp
            1140                1145                1150

Phe Ser Gln Val Tyr Lys Asn Ser Glu Leu Tyr Gln Arg Asn Lys Arg
        1155                1160                1165

Leu Ile Gln Glu Leu Ser Asn Pro Pro Gly Ser Ser Asp Leu Tyr
    1170                1175                1180

Phe Pro Thr Gln Tyr Ser Gln Pro Met Ala Val Gln Cys Met Ala Cys
1185                1190                1195                1200

Leu Trp Lys Gln His Leu Ser Tyr Trp Arg Asn Pro Pro Tyr Thr Ala
            1205                1210                1215

Val Arg Phe Phe Phe Thr Thr Ile Ile Ala Leu Leu Phe Gly Thr Ile
            1220                1225                1230

Phe Trp Asp Leu Gly Ser Lys Thr Ser Lys Lys Ile Asp Leu Phe Asn
            1235                1240                1245

Ala Met Gly Ser Met Tyr Ala Ala Val Ile Phe Ile Gly Val Gln Asn
        1250                1255                1260

Cys Ser Ser Val Gln Pro Val Val Ala Val Glu Arg Thr Val Phe Tyr
1265                1270                1275                1280

Arg Glu Arg Ala Ala Gly Met Tyr Ser Ala Leu Pro Tyr Ala Phe Gly
            1285                1290                1295

Gln Val Val Ile Glu Leu Pro Tyr Val Leu Ile Gln Ser Ile Leu Tyr
        1300                1305                1310

Gly Val Ile Val Tyr Ala Met Ile Gly Phe Glu Trp Thr Val Ala Lys
        1315                1320                1325

Phe Phe Trp Tyr Ile Phe Phe Met Tyr Phe Thr Leu Leu Tyr Phe Thr
    1330                1335                1340

Phe Tyr Gly Met Met Thr Val Gly Ile Thr Pro Asn His Asn Ile Ala
1345                1350                1355                1360

Ala Ile Val Ser Ala Ala Phe Tyr Gly Leu Trp Asn Leu Phe Ser Gly
            1365                1370                1375

Phe Ile Val Pro Arg Pro Arg Ile Pro Ile Trp Trp Arg Trp Tyr Tyr
            1380                1385                1390

Trp Ala Cys Pro Val Ala Trp Thr Leu Tyr Gly Leu Val Thr Ser Gln
        1395                1400                1405

Phe Gly Asp Ile Glu Glu Arg Leu Glu Asp Thr Gly Glu Val Val Ser
    1410                1415                1420

Asp Phe Leu Arg Ser Tyr Phe Gly Phe Lys His Ser Phe Leu Gly Val
1425                1430                1435                1440

Val Ala Val Met Val Val Ala Phe Pro Leu Leu Phe Ala Phe Leu Phe
            1445                1450                1455

Ala Phe Ser Ile Lys Met Leu Asn Phe Gln Lys Arg
```

1460           1465

<210> SEQ ID NO 4
<211> LENGTH: 4760
<212> TYPE: DNA
<213> ORGANISM: banana
<220> FEATURE:
<223> OTHER INFORMATION: Musa spp cv Hsien Jin Chiao AAA group

<400> SEQUENCE: 4

| | | | | | | |
|---|---|---|---|---|---|---|
| agctgatctg | tggtaactga | gcagaagaag | agggaagatg | tcagctctga | ccggtcacac | 60 |
| acttggaaac | ttcgtccctt | tacttgggat | gtcagtttgt | agcatggaga | gtagtagtaa | 120 |
| gcaccgctac | ggctgtgtca | ctctataaga | tctctcttcc | gtctctctcc | tactctttgc | 180 |
| gggagatcat | tcgaccggag | tttggttggg | ggagatggag | ccgagcgagg | tgctcaggat | 240 |
| agggagcctg | cgaaggaaca | gttcggtatg | gaggagaggg | gacgagagca | tcttctcgcg | 300 |
| gtcgtcgcgg | gacgaggacg | acgaggaggc | actcaagtgg | gccgccctcg | agaagctgcc | 360 |
| caccttcgac | cgcgtccgcc | ggggcatcct | ggcgctggcg | gaggatggtg | gcgagctgca | 420 |
| ggaagtcaat | atcgagaggc | ttggcttccg | ggagaagaaa | gcccttatcg | aacgcctcgt | 480 |
| tcgtgtcgcc | gacgaggaca | cgagcgcgtt | cttgctcaag | ctcagggatc | gcgtcgaccg | 540 |
| agtcgggatt | gatctgccca | ccatagaagt | ccgatatgag | cacctcagca | tcgaagcaga | 600 |
| gacgtatgtg | ggtaacagag | gattgcctac | catcttcaat | tccacccttta | acatgctaga | 660 |
| ggcctttgga | aattacttgc | gagtactacc | aagcagaaag | agacctttgt | cgatccttca | 720 |
| tgatgtcagc | ggaatcatca | aacctcgcac | gatggctttg | ctcttaggtc | ctccgggatc | 780 |
| gggaaaaacc | acgctgttgt | tggctttggc | tggaaagctc | agctctgatc | tcaaggttac | 840 |
| cggaaaagtg | acctacaatg | gccatgacat | gagtgaattc | gtccctcaaa | gaaccgctgc | 900 |
| gtacatcagc | cagtatgacc | ttcacatcgg | ggagatgaca | gtccgcgaga | cgctagcttt | 960 |
| ctctgccagg | tgccaaggag | taggcactcg | ttacgagatg | ttgactgagc | tcgccaggag | 1020 |
| agagaaggcc | gcaaacatca | agccagatcc | ggacattgat | gtgttcatga | aggcgtcttc | 1080 |
| gatgaaaggg | caagaagcca | atgtgatcac | ggagtatatc | ctgaagatcc | tcggtctgga | 1140 |
| ggtctgcgcc | gacaccatgg | taggagatga | gatgttgaga | ggaatctccg | gtggtcagag | 1200 |
| gaagcgtgtc | acgacaggtg | agatgcttgt | tgggccagcg | agagctctgt | tcatggacga | 1260 |
| gatatcaacc | ggtctggata | gctcgactac | tttccagata | gtgaactcgc | tcaggcaaac | 1320 |
| cattcacatt | cttagtggaa | ctgcgatgat | ttccctgctg | cagcccgcac | cggagacata | 1380 |
| cgacctttc | gacgacatca | ttcttctctc | cgatggcctc | atcgtgtatc | aaggtcctcg | 1440 |
| tgacaatgtg | ctcgagttct | tcgaatccat | gggcttcaga | tgccccgagc | ggaagggtgt | 1500 |
| tgcggacttc | ctacaagaag | tgacatcgag | gaaggatcag | caacagtact | gggctcggca | 1560 |
| ggacgaacct | tacagatacg | tgcctgtgag | agaatttgca | gaggcattcc | agtccttcca | 1620 |
| tgtcggtcga | gccttggggg | acgaactctc | tgtccccttc | gacaagacca | agagccatcc | 1680 |
| tgctgctctg | acgaccacaa | gatatgggt | tagcaagaag | gaagtgttga | aggctaacat | 1740 |
| cgacagagaa | ctgctgctga | tgaagaggaa | ctcgttcgtc | tacatcttca | aggcgaccca | 1800 |
| acttaccatc | atggcaatcg | tttccatgac | cgtcttcctg | cgtactaaga | tgcctcggga | 1860 |
| gacggaaacc | gatggggttga | cctatttggg | ggcactgttc | ttttcggtgg | tcatggtcat | 1920 |
| gttcaatggg | ttctctgaac | tcgccatgac | catcatgaag | cttcctgtct | tcttcaagca | 1980 |
| aagagaccctc | ctcttctatc | cggcatggtc | atacacgata | ccgacatgga | ttctcaagat | 2040 |

```
tcccatcgca tttgttgaag ttgcagtgtg ggttttcaca acctattatg tcatcggatt    2100
cgatccaaat gtcggaaggc tgttcaagca atatctgctg cttctgggga taactcagat    2160
ggcatctgcc gtcttccgaa ccatcggggc attaggtagg aacatgatcg ttgcaaacac    2220
ctttgcgtcg ctttcgctgc tcattcttct cgtgctgggt ggcttcattc tttcacgaga    2280
acaagtgaag aaatggtgga tttggggata ctggatctcg ccactgacct acgcacagaa    2340
cgcgatatca gtgaatgaat tcatgggcaa caactggaag catactgctc caggatcgaa    2400
cgagtcgctg ggcgtccgag tgttgaagtc acgtggagtc ttcccggaag caagatggta    2460
ttggatcggc tttggggctt tggttggcta cgtacttctg ttcaatgctc tgttcactct    2520
ggctctcagc tatctcgatc cctttggaaa atctcagccg cctatttctg aggagacttt    2580
gaaggaaaaa cacatcaatc taaccggaga aggattagag tcatcatcca gaggaaggaa    2640
atctatagat cactctgcat ccaagagcaa gtcccgtgga catgccaagt caatgctctc    2700
taaatctcgg cgtgcgggta gcgagaatgg aatgaggagg aaggacagct cattgggttc    2760
catgaaggca gctttcgatc agaacagaag gggaatggtc ctcccttca ccccgctttc     2820
catcaccttc gatgatataa gatactctgt cgacatgcct caggaaatga agctcaagg     2880
tgtggcggaa gaccgcttgg agctcctcaa gggtgtgagt ggatctttca ggccaggtgt    2940
gctcacggcg ctgatgggcg taagcggagc cgggaagacg acgctgatgg atgtgctggc    3000
tgggagaaag accgggggat acatcgaagg aaacattaac atctccggct accctaagaa    3060
gcaggagacc tttgctcgca tatcaggata ctgcgaacag aatgacatcc actctcctca    3120
cgtcacggtt tacgagtcca tcgtctactc cgcctggctt cggctacctc ctgaggtcga    3180
ttctgaaaca aggaagatgt tcgtcgacga ggtcatggag cttgtggagc tgacgccact    3240
gagggatgcg ctggttgggt tgccaggagt cgatgggcta tcgaccgagc aaaggaagag    3300
gttgaccatc gccgtggagc tggtcgccaa cccatccatc atattcatgg atgaacccac    3360
ctctgggctc gacgcaaggg ctgcggccat cgtcatgagg accgtgagga acacggtgga    3420
caccgggagg acgtggtgt gcaccattca ccaacccagc atcgacatat tcgaagcttt     3480
cgatgagctc ttcctattga agcgaggtgg agaaagata tacgcaggtc ccctcggtcg     3540
ccattcttgc catctgatcg attattttga gggaatcaat ggtgtcagca agataaagga    3600
tggttacaac cccgcgacat ggatgttgga agtgacgaca caggcgcaag aaggcatact    3660
gggtgtcgac ttcagccaag tatacaagaa ctcggagctc taccagagaa acaagaggtt    3720
gatccaggaa ctgagcaatc ctcctccggg ttcgagtgat ctctacttcc caacgcagta    3780
ctctcaacca atggccgtgc aatgcatggc gtgcctgtgg aaacagcact tgtcatactg    3840
gaggaaccct ccgtataccg ccgtgaggtt cttcttcaca accatcatcg ctctgctgtt    3900
tggcaccata ttttgggacc tcggctccaa aacatcgaag aaaatagatc tgttcaatgc    3960
tatgggttcc atgtacgccg ctgtcatctt catcggggtg cagaactgct cctccgttca    4020
accggtggtg gccgtcgaac gaacggtctt ttacagggag agagcagctg gaatgtactc    4080
agctctgccg tatgcgtttg gacaagtggt gatcgagcta ccgtacgttc tgatccagtc    4140
gatcctatat ggtgtgatcg tgtacgccat gattggcttc gagtggactg ttgctaagtt    4200
cttctggtac atattcttca tgtacttcac cctcctctac ttcacgttct acggaatgat    4260
gacggtgggg atcactccca accacaacat cgccgccatc gtctctgctg ccttctacgg    4320
actatggaat ctcttctccg gattcatcgt cccacgacct agaatcccga tatggtggag    4380
atggtactac tgggcatgtc ctgtagcttg gaccttgtat ggattggtca cctcacagtt    4440
```

| | |
|---|---|
| cggtgatata gaggagagac tcgaggacac cggcgaggtc gtgtcggatt tcttgaggag | 4500 |
| ttacttcggg ttcaagcata gcttcttggg ggtggtagct gtgatggtgg tggcgtttcc | 4560 |
| tctgctcttt gctttcctct ttgcattctc cattaagatg ctcaacttcc aaaagagatg | 4620 |
| aagatggcag tgcctgccaa acaccaaaat atttctgtga tcatagatag ataatttggg | 4680 |
| gatatgtatg cggtttgatg atgaagacaa ctctgtgagt cattcttaca tacaattatg | 4740 |
| aagcaggtta tttggcagca | 4760 |

```
<210> SEQ ID NO 5
<211> LENGTH: 27
<212> TYPE: DNA
<213> ORGANISM: artificial sequence
<220> FEATURE:
<223> OTHER INFORMATION: forward primer

<400> SEQUENCE: 5
tcctctagaa tggaaccgag cgaggtg                                     27

<210> SEQ ID NO 6
<211> LENGTH: 28
<212> TYPE: DNA
<213> ORGANISM: artificial sequence
<220> FEATURE:
<223> OTHER INFORMATION: reverse primer

<400> SEQUENCE: 6
agcggtacct catctcttct ggaagttg                                    28

<210> SEQ ID NO 7
<211> LENGTH: 27
<212> TYPE: DNA
<213> ORGANISM: artificial sequence
<220> FEATURE:
<223> OTHER INFORMATION: forward primer

<400> SEQUENCE: 7
tcctctagaa tggagccgag cgaggtg                                     27

<210> SEQ ID NO 8
<211> LENGTH: 28
<212> TYPE: DNA
<213> ORGANISM: artificial sequence
<220> FEATURE:
<223> OTHER INFORMATION: reverse primer

<400> SEQUENCE: 8
agcggtacct catctctttt ggaagttg                                    28

<210> SEQ ID NO 9
<211> LENGTH: 16
<212> TYPE: DNA
<213> ORGANISM: artificial sequence
<220> FEATURE:
<223> OTHER INFORMATION: forward primer

<400> SEQUENCE: 9
atggagccga gcgagg                                                 16

<210> SEQ ID NO 10
<211> LENGTH: 19
<212> TYPE: DNA
<213> ORGANISM: artificial sequence
<220> FEATURE:
<223> OTHER INFORMATION: reverse primer
```

-continued

```
<400> SEQUENCE: 10
ggcctctagc atgttaagg                                                     19
```